United States Patent
Kandori

(10) Patent No.: US 9,719,847 B2
(45) Date of Patent: Aug. 1, 2017

(54) DETECTION CIRCUIT, DRIVING METHOD, PROBE, AND SUBJECT INFORMATION ACQUIRING APPARATUS

(71) Applicant: CANON KABUSHIKI KAISHA, Tokyo (JP)

(72) Inventor: Atsushi Kandori, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 376 days.

(21) Appl. No.: 14/200,904

(22) Filed: Mar. 7, 2014

(65) Prior Publication Data
US 2014/0251017 A1  Sep. 11, 2014

(30) Foreign Application Priority Data

Mar. 9, 2013 (JP) ................. 2013-047423
Feb. 5, 2014 (JP) ................. 2014-019964

(51) Int. Cl.
| | |
|---|---|
| G01H 11/08 | (2006.01) |
| G01H 11/06 | (2006.01) |
| G01N 29/24 | (2006.01) |
| G01S 7/52 | (2006.01) |
| G01N 29/38 | (2006.01) |
| A61B 8/00 | (2006.01) |
| G01H 3/12 | (2006.01) |
| A61B 5/00 | (2006.01) |

(52) U.S. Cl.
CPC ............. *G01H 11/08* (2013.01); *G01H 11/06* (2013.01); *G01N 29/2406* (2013.01); *G01N 29/2418* (2013.01); *G01N 29/38* (2013.01); *G01S 7/52025* (2013.01); *A61B 5/0095* (2013.01); *A61B 8/54* (2013.01); *G01H 3/12* (2013.01); *G01S 7/52096* (2013.01)

(58) Field of Classification Search
CPC .......... G01H 11/08; G01H 11/06; G01H 3/12; G01N 29/38; G01N 29/2418; G01N 29/2406; G01S 7/52025; G01S 7/52096; A61B 5/0095
USPC .......................................................... 73/661
See application file for complete search history.

(56) References Cited

U.S. PATENT DOCUMENTS

| | | | | |
|---|---|---|---|---|
| 4,816,713 A * | 3/1989 | Change, Jr. | ................ | G01L 9/08 310/319 |
| 5,603,324 A | 2/1997 | Oppelt | | |
| 5,724,312 A | 3/1998 | Oppelt | | |
| 6,567,572 B2 * | 5/2003 | Degertekin | .............. | G01D 5/38 250/237 G |

(Continued)

FOREIGN PATENT DOCUMENTS

| | | |
|---|---|---|
| EP | 1762181 A1 | 3/2007 |
| JP | 2011-193978 A | 10/2011 |

(Continued)

OTHER PUBLICATIONS

Improving ultrasound imaging with integrated electronics (Ultrasonics Symposium (IUS), 2009 IEEE International) :2718-2721.

*Primary Examiner* — J M Saint Surin
(74) *Attorney, Agent, or Firm* — Canon U.S.A., Inc. IP Division

(57) ABSTRACT

A detection circuit detects a signal output from an element that receives an acoustic wave. The detection circuit is configured so as not to conduct a detection operation during a period in which the element does not receive the acoustic wave.

22 Claims, 23 Drawing Sheets

(56) References Cited

U.S. PATENT DOCUMENTS

| | | | | |
|---|---|---|---|---|
| 8,891,334 B2* | 11/2014 | Degertekin | ........... | G01S 7/5202 367/137 |
| 9,238,250 B2* | 1/2016 | Kandori | ................ | B06B 1/0292 |
| 2002/0165585 A1* | 11/2002 | Dupelle | ................... | A61N 1/39 607/5 |
| 2008/0015437 A1 | 1/2008 | Hongou | | |
| 2011/0227448 A1 | 9/2011 | Kandori | | |
| 2012/0310096 A1 | 12/2012 | Hongou | | |

FOREIGN PATENT DOCUMENTS

| | | |
|---|---|---|
| JP | 2011-229556 A | 11/2011 |
| JP | 2013-90650 A | 5/2013 |

* cited by examiner

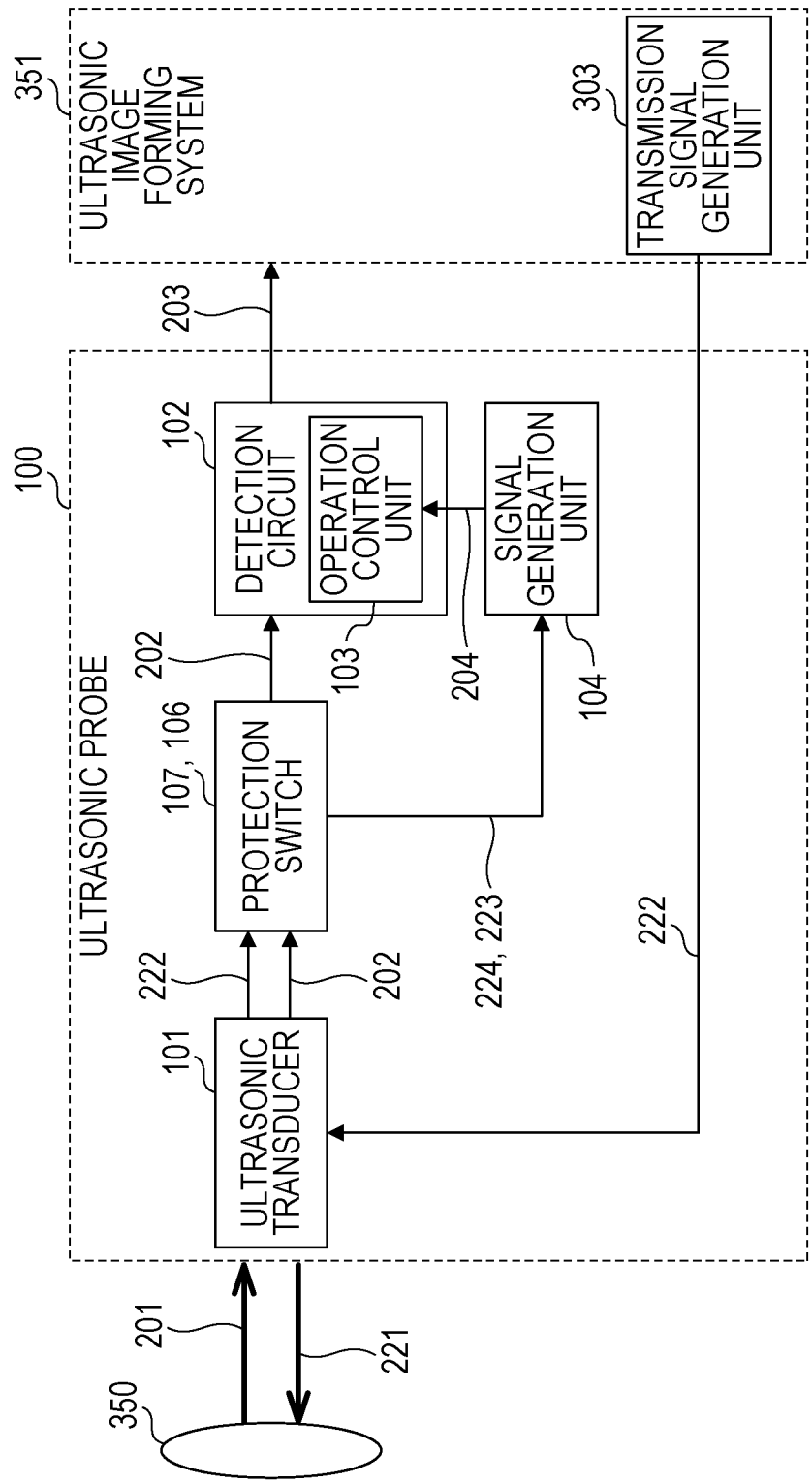

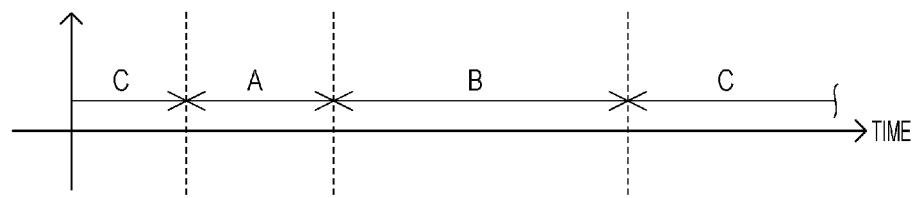
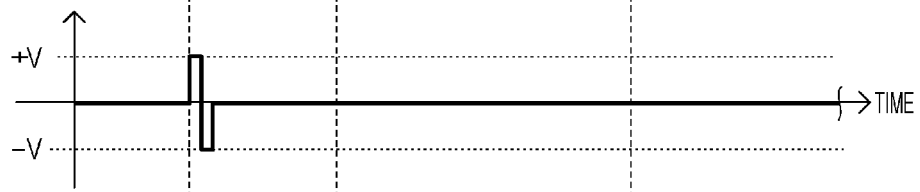
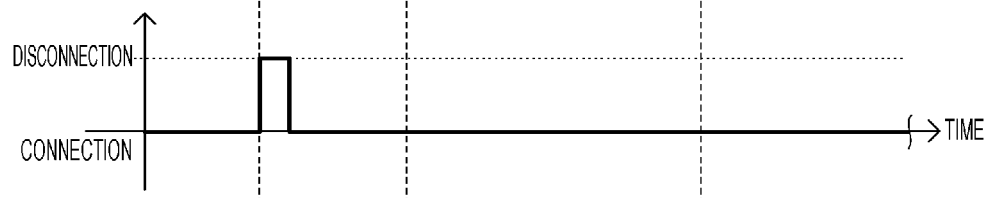
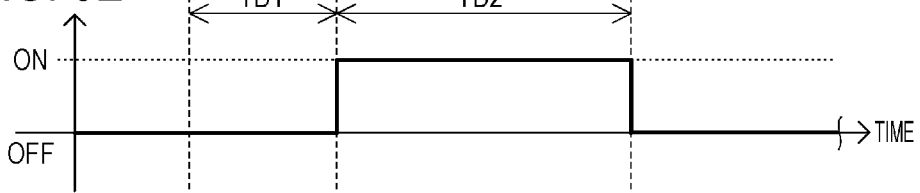
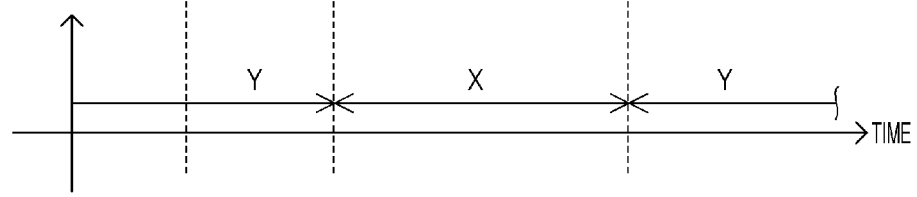

DETECTION CIRCUIT, DRIVING METHOD, PROBE, AND SUBJECT INFORMATION ACQUIRING APPARATUS

BACKGROUND OF THE INVENTION

Field of the Invention

The present disclosure relates to a detection circuit for an electromechanical transducer that performs a reception of an acoustic wave such as an ultrasonic wave (hereinafter, which may simply be referred to as transducer or the like in some cases), and a driving method for the detection circuit, a probe, and a subject information acquiring apparatus. In the present specification, the acoustic wave includes an elastic wave such as photoacoustic wave, optical ultrasonic wave, sound wave, or ultrasonic wave, and the acoustic wave generated by light irradiation is particularly called "photoacoustic wave". The acoustic wave transmitted from the probe among the acoustic waves may be called "ultrasonic wave", and a wave obtained while the transmitted ultrasonic wave is reflected in the subject may particularly be called "reflected wave" in some cases. The term "ultrasonic wave" may be used to represent the acoustic wave in some cases.

Description of the Related Art

A piezoelectric element (PZT), a polymer molecule film (PolyVinylidene DiFluoride (PVDF)), or the like is used for a transmission and reception transducer for generating and detecting the ultrasonic wave. The "transmission and reception" mentioned in the present specification mean at least one of the transmission and the reception. Transducers that include a built-in preamplifier (voltage amplification circuit) are proposed to improve an S/N ratio of these transducers at the time of the ultrasonic wave detection (see Improving ultrasound imaging with integrated electronics (Ultrasonics Symposium (IUS), 2009 IEEE International): 2718-2721). In addition, a capacitive-micromachined-ultrasonic-transducer (CMUT) serving as an electrostatic capacitance type ultrasonic transducer is proposed. The CMUT is fabricated by using a micro-electro-mechanical-systems (MEMS) process in which a semiconductor processing is adapted. The CMUT includes a current-voltage conversion circuit to convert a current signal into a voltage signal at the time of the ultrasonic wave detection. FIG. 13 illustrates an arrangement in this circuit where an ultrasonic probe 100, an ultrasonic transducer 101, a detection circuit 102, a reception ultrasonic wave 201, a detection signal 202, and a detection output signal 203 are arranged.

According to the configuration in which the preamplifier or the current-voltage conversion circuit is built in the ultrasonic probe, a new problem of heat generation in the preamplifier or the current-voltage conversion circuit occurs. The probe includes a plurality of elements configured to transmit or receive the ultrasonic wave, and also a restriction exists on an upper limit of the heat amount that can be released from the probe. Therefore, a temperature of the probe as a whole is increased by the heat generation. The increase in the probe temperature leads to a problem particularly in a case where the probe is used while being contacted against a human body. In addition, a characteristic of the probe may be changed because of the temperature increase, and parts in contact with the probe may be affected in some cases.

SUMMARY OF THE INVENTION

In view of the above-described problem, an embodiment of the present invention provides a detection circuit configured to conduct a detection operation for detecting a signal output from an element that is configured to receive an acoustic wave, in which the detection operation is not conducted during a period in which the element does not receive the acoustic wave.

Further features and aspects of the present invention will become apparent from the following description of exemplary embodiments with reference to the attached drawings.

BRIEF DESCRIPTION OF THE DRAWINGS

FIGS. 6A to 6F are explanatory diagrams for describing a sixth exemplary embodiment.

DESCRIPTION OF THE EMBODIMENTS

An important point in an aspect of the present invention resides in that during a period in which an element in a transducer does not receive an acoustic wave, a detection circuit has a current consumption significantly lower than a normal current consumption (establishing a state in which a detection circuit operation is stopped). The above-described detection circuit can be provided in a probe configured to transmit and receive the acoustic wave together with the transducer.

Hereinafter, exemplary embodiments of the present invention including a detection circuit, an ultrasonic probe, and the like will be described in detail by using the drawings.

First Exemplary Embodiment

Figure 1A:
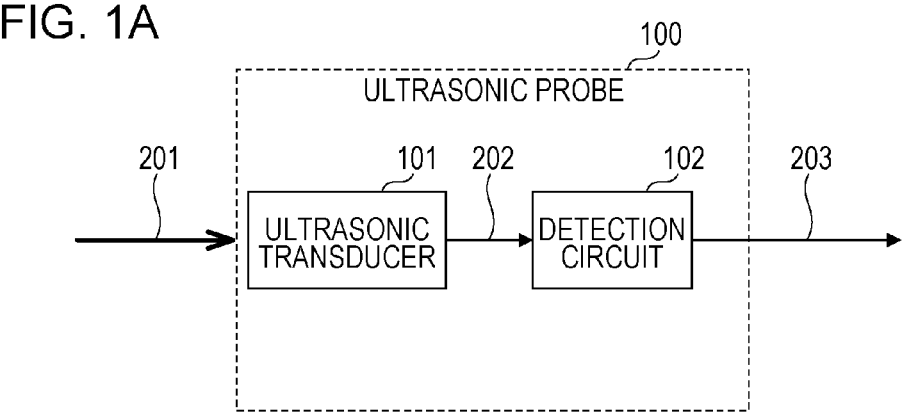
FIGS. 1A to 1C are explanatory diagrams for describing a detection circuit and an ultrasonic probe according to a first exemplary embodiment.

FIG. 1A is an explanatory diagram for describing a configuration of the ultrasonic probe according to the present exemplary embodiment. In FIG. 1A, an ultrasonic probe 100, an ultrasonic transducer 101, a detection circuit 102, a reception ultrasonic wave 201, a detection signal 202, and a detection output signal 203 are illustrated. When the transducer 101 receives the ultrasonic wave 201, the detection signal 202 is output from the transducer 101 and input to the detection circuit 102. Since the detection signal 202 is an extremely faint signal, the detection signal 202 is converted into a signal to be output to an external part by the detection circuit 102 and is output as the detection output signal 203.

Figure 1B:
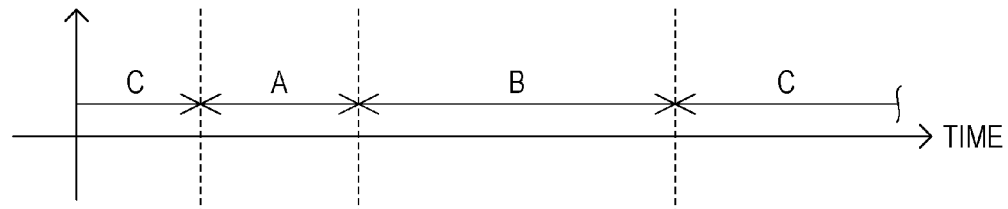
Figure 1C:
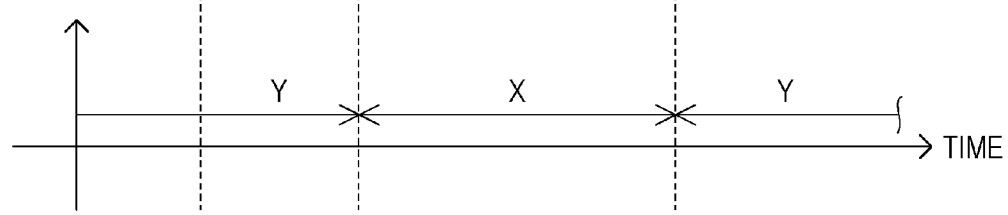

FIGS. 1B and 1C are explanatory diagrams for describing operations conducted by the detection circuit 102 and the ultrasonic probe 100 according to the present exemplary embodiment. FIG. 1B represents a period for each operation mode of the ultrasonic probe 100. FIG. 1C represents an operation period of the detection circuit 102. Each of the horizontal axes represents time. The operation period of the ultrasonic probe 100 is composed of a period (A) in which the ultrasonic wave is generated (transmitted), a period (B) in which the ultrasonic wave is received by the transducer 101, and a remaining period (C) in which neither the transmission nor the reception is not conducted. Since the ultrasonic wave is transmitted within a substance at a certain velocity, if a distance from the transducer 101 in a range where the object to be inspected exists and a type of the substance (that is, a velocity depending on this substance) are determined, it is possible to find out a period during which the ultrasonic wave reaches the transducer 101. When this period is set as the reception period (B), the detection output signal is not used during a period other than this reception period (B), and the detection output signal 203 may not be output from the detection circuit 102.

According to the aspect of the present invention, to focus attention on this state, the detection circuit 102 does not conduct the signal detection operation (corresponding to period Y) in the periods (A and C) other than the reception period (B). With this configuration, while the detection circuit 102 conducts the detection operation (corresponding to a period X) during the reception period (B), it is also possible to shorten the period (X) during which the detection circuit 102 is operated. Since the power consumption of the detection circuit 102 corresponds to the period (X) during which the detection circuit 102 is operated, as the operation period is shortened, the power consumption is also decreased. While the power consumption is decreased, it is possible to reduce the heat generation from the detection circuit 102. Since the above-described technical spirit is employed, it is possible to reduce the heat generation from the detection circuit 102 without imparting the influence on the reception operation. With this configuration, it is possible to provide the apparatus such as the ultrasonic probe including the detection circuit where the temperature increase hardly occurs. According to the present exemplary embodiment, the detection circuit 102 is previously set in a manner that the detection circuit 102 does not perform the signal detection operation during the period Y on the basis of the ultrasonic wave reach period to the transducer 101 found out from the range where the object exists and the type of the substance.

The transducer 101 that can be used in an embodiment of the present invention can also use the CMUT serving as the electrostatic capacitance type transducer. The CMUT has a frequency band broader than the above-described voltage output type transducer and at the time of the reception of the ultrasonic wave, outputs a current signal corresponding to the received ultrasonic wave. To elaborate, a current output type element is provided. Since this current signal is faint and easily deteriorated at the time of the signal transmission, the current signal is converted to a voltage signal by a current-voltage conversion circuit and is output from the probe. In this manner, in the CMUT, the detection circuit (current-voltage conversion circuit) has to be arranged to be close to the CMUT. For that reason, with the application of an embodiment of the present invention, even in a case where the detection circuit is arranged so as to be close to the CMUT in the configuration using the CMUT, the heat generation amount of the detection circuit can be suppressed to a low level, and it is possible to provide the broad band ultrasonic probe with the stable characteristic in which the influence from the heat from the detection circuit is hardly imparted on the CMUT characteristic.

In addition, since the CMUT is provided with the element using the electrostatic capacitance, the characteristic is easily affected with respect to a parasitic capacitance of a wiring part. For that reason, a transimpedance circuit in which an influence from the parasitic capacitance is hardly received may be used for the detection circuit serving as the current-voltage conversion circuit. However, to reduce the influence from the parasitic capacitance, the transimpedance circuit is set to respond at a high speed to a high frequency as compared with a normal voltage amplification circuit, and the power consumption is increased. By applying an embodiment of the present invention to the configuration in which this CMUT and the transimpedance circuit are used, it is possible to provide the broad band ultrasonic probe in which the characteristic is stable since the influence from the parasitic capacitance of the wiring is hardly received and also the generated heat is low.

Figure 9:
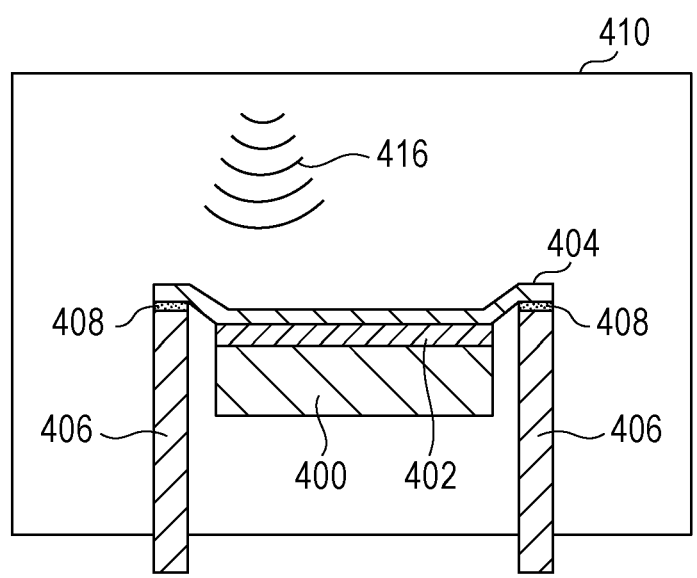
FIG. 9 is an explanatory diagram for describing an example of the ultrasonic probe.

An example of the electrostatic capacitance type transducer and an example of the current-voltage conversion circuit will be described. FIG. 9 is a schematic diagram of a probe tip portion using the electrostatic capacitance type transducer. In the probe tip portion, a device substrate 400 on which the CMUT 402 is arranged as an ultrasonic wave sensor that receives an ultrasonic wave 416 and a protection layer 404 for the CMUT are contained in a case 406. The case 406 and the protection layer 404 are sealed by an adhesive agent 408, so that an acoustic medium 410 does not penetrate into the case 406. The present invention is not limited to this configuration, and a configuration in which only the protection layer is provided on the sensor surface may also be adopted. In case of the probe configured to perform the transmission and reception of the ultrasonic wave, a general acoustic lens is preferably provided to a front surface of the CMUT (on the subject side).

Figure 10A:
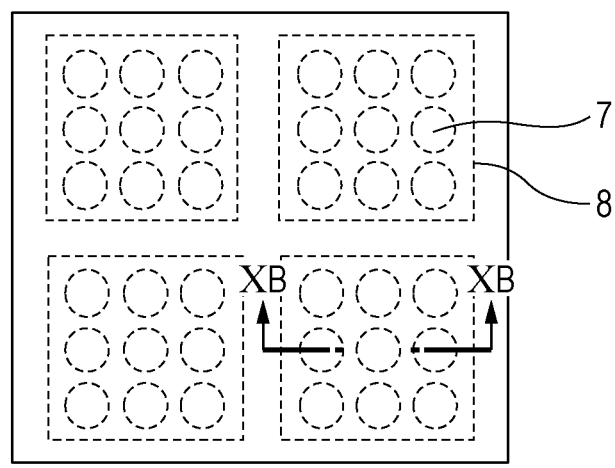
FIGS. 10A and 10B are explanatory diagrams for describing an example of an electrostatic capacitance type transducer.
Figure 10B:
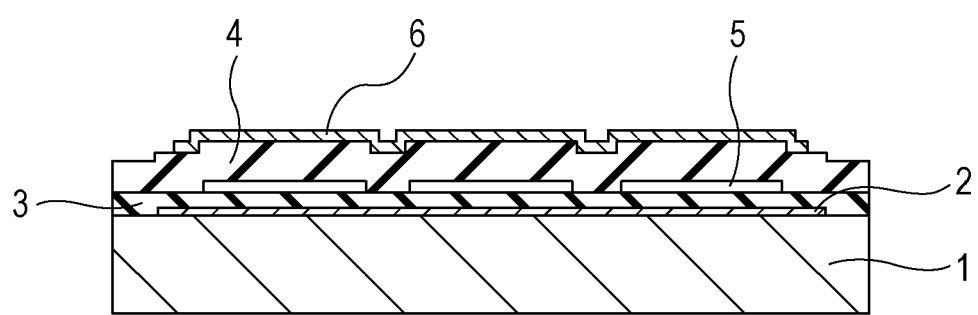

FIG. 10A is a top view of an example of the CMUT including an element that includes a plurality of cells, and FIG. 10B is an XB-XB cross sectional diagram of FIG. 10A. This probe includes a plurality of elements 8, and each of the elements 8 includes cells 7. In FIG. 10A, each of the four elements 8 includes nice cell structures 7, but any number of elements and any number of cell structures may be used. As illustrated in FIG. 10B, the cell 7 in the present example is composed of a substrate 1, a first electrode (lower electrode) 2, an insulating film 3 on the first electrode 2, a chamber 5 such as a gap, a vibration membrane 4, and a second electrode (upper electrode) 6 on the vibration membrane 4. The substrate 1 is made of Si, but an insulating substrate such as glass may be employed. The first electrode 2 is formed of a metallic thin film such as titanium or aluminum. In a case where the substrate 1 is formed by low resistance silicon, the substrate 1 itself can be used as the first electrode 2. The insulating film 3 can be formed by depositing a thin film made of silicon oxide or the like. The vibration membrane 4 and a vibration membrane support member are formed by depositing a thin film made of silicon nitride or the like. The second electrode 6 can be formed by a metallic thin film made of titanium, aluminum, or the like. Since the cell 7 is provided with the first electrode 2 and the second electrode 6 arranged so as to sandwich the chamber 5, a direct voltage is applied to the first electrode 2 or the second electrode 6 to receive the acoustic wave. When the acoustic wave is received, the vibration membrane 4 is deformed, and a distance (height) of the gap is changed, so that the electrostatic capacitance between the electrodes is changed. It is possible to detect the acoustic wave by detecting this electrostatic capacitance changed from the first electrode 2 or the second electrode 6. The element can also transmit the acoustic wave by applying an alternating voltage to the first electrode 2 or the second electrode 6 to vibrate the vibration membrane 4.

Figure 11A:
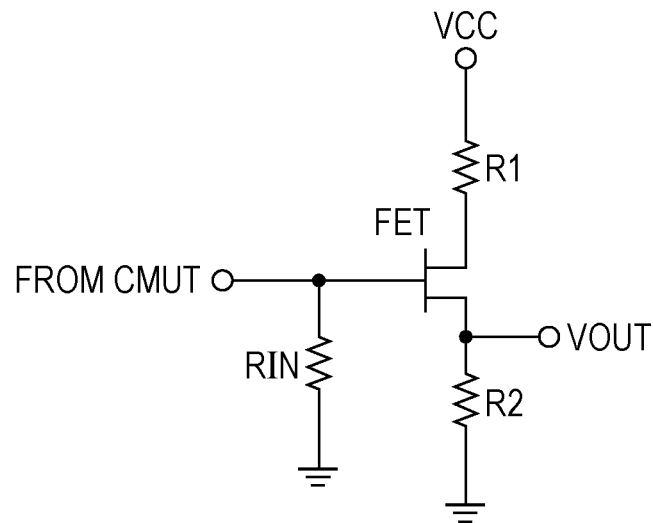
FIGS. 11A to 11D are explanatory diagrams for describing an example of a current-voltage conversion circuit connected to the electrostatic capacitance type transducer.
Figure 11B:
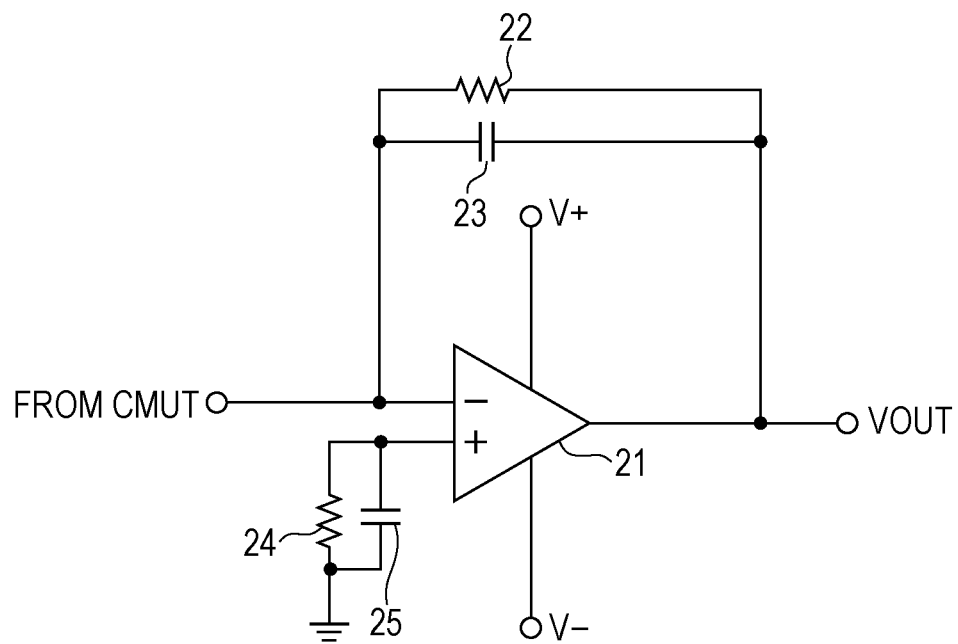
Figure 11C:
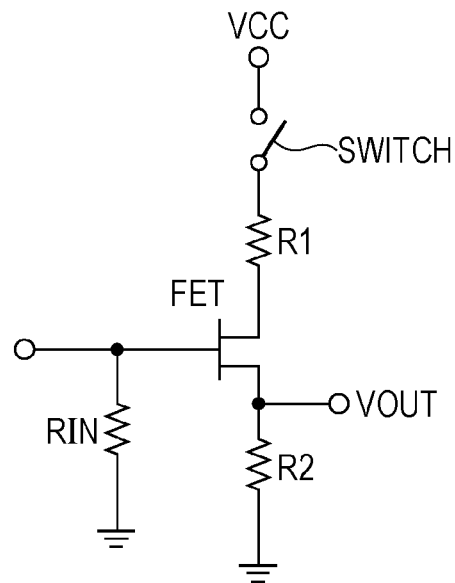
Figure 11D:
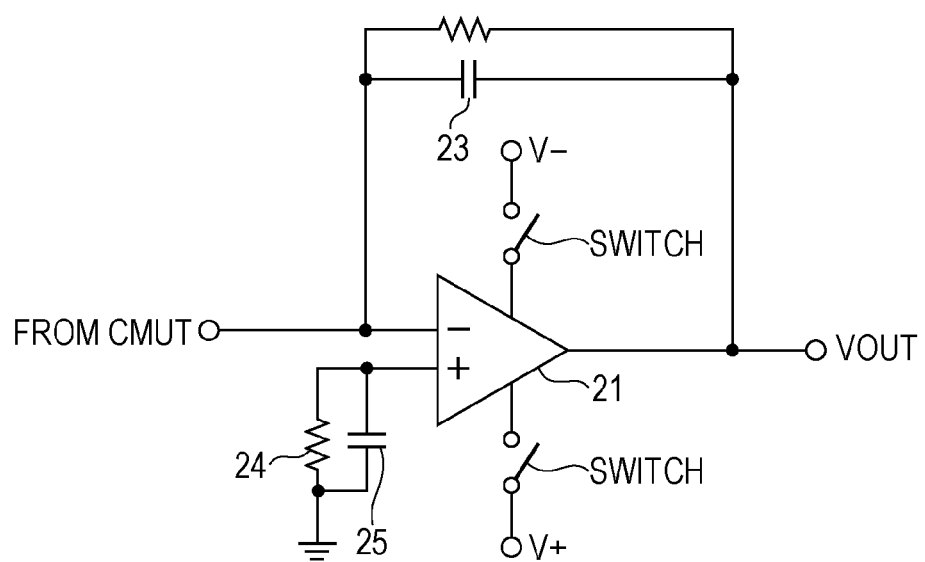

FIGS. 11A to 11D are explanatory diagrams for describing an FET source follower circuit using a high resistance (which is illustrated in FIG. 11A) corresponding to an example of the detection circuit of the amplifier unit in the first stage configured to perform the current-voltage conversion and also describing the transimpedance circuit. In the transimpedance circuit of FIG. 11B, an operation amplifier 21, resistances 22 and 24, and capacitors 23 and 25 are arranged. This detection circuit is configured to detect a faint current generated by the vibration of the vibration membrane 4 from the first electrode 2 or the second electrode 6. The operation amplifier 21 is connected to positive and negative power supplies VDD and VSS (not illustrated). An inverting input terminal (−IN) of the operation amplifier 21 is connected to a wiring of the detection electrode (the first electrode 2 or the second electrode 6) of the CMUT. An output terminal (VOUT) of the operation amplifier 21 is connected to the inverting input terminal (−IN) via the resistance 22 and the capacitor 23 which are connected in parallel, and the output signal is fed back. A non-inverting input terminal (+IN) of the operation amplifier 201 is connected to a ground terminal (GND) by the resistance 24 and the capacitor 25 which are connected in parallel. A voltage of the ground terminal (GND) is an intermediate potential between the positive power supply VDD and the negative power supply VSS. Resistance values of the resistance 22 and capacitance values of the resistance 24 and the capacitor 23 and the capacitor 25 are respectively the same values. A current change from the detection electrode is converted to a voltage value corresponding to the current change by the transimpedance circuit and is then output. The transimpedance circuit has a characteristic with which a broad band region can be obtained as compared with the other circuit configuration (such as the FET source follower circuit using the high resistance). Since the output signal from the detection circuit is output as a voltage value, the signal degradation hardly occurs in a wiring extending after the detection circuit. The transimpedance circuit is a circuit with which a high-speed and high-gain current-voltage conversion can be realized by using the broad band operation amplifier. To construct the detection circuit according to the exemplary embodiment of the present invention, for example, an ON/OFF switch (see FIGS. 11C and 11D) is provided at a location of a VCC terminal of the above-described FET source follower circuit, a V+ terminal or a V− terminal of the transimpedance circuit, or the like, and this ON/OFF switch is controlled by a detection circuit operation control unit 103 which will be described below.

Figure 14A:
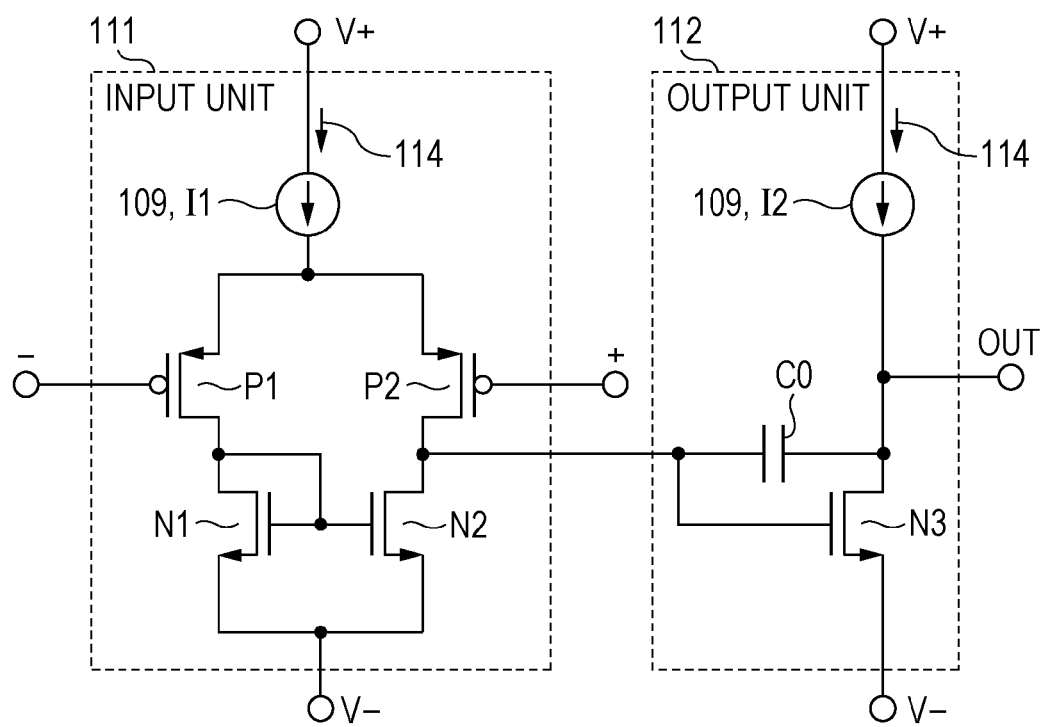
FIGS. 14A and 14B are circuit frame formats of an internal part of an operation amplifier used in a transimpedance circuit serving as a detection circuit of a CMUT.
Figure 14B:
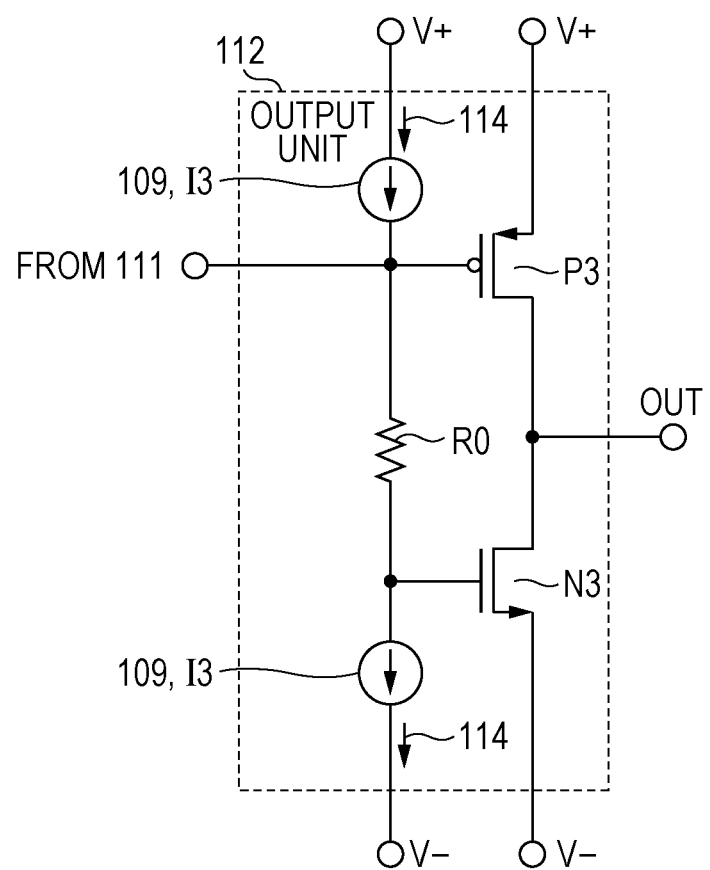

FIGS. 14A and 14B illustrate a circuit frame format inside an operation amplifier used in the transimpedance circuit. The operation amplifier is composed of an input unit 111 configured to amplify a faint signal and an output unit 112 having a capacity of driving an external load. In FIGS. 14A and 14B, P-type MOS transistors P1 to P3, N-type MOS transistors N1 to N3, constant current sources I1 to I3, a capacitance C0 for a phase compensation, and a resistance R0 for generating a constant voltage are illustrated.

The input unit 111 can be composed of a general differential amplifier circuit. In FIG. 14A, a single output of the differential amplifier circuit is described as an example, but the present invention is not limited to this. Any of the differential amplifier circuit of a differential output type, the differential amplifier circuit of a multistage structure, and the like can be employed so long as the circuit can be used for the input unit of the operation amplifier, and a similar effect can be attained.

The output unit 112 can also be composed of an output circuit of a general operation amplifier. In FIG. 14A, a configuration of a class A amplifier has been described as an example, but the present invention is not limited to this. For example, in addition to a class AB amplifier illustrated in FIG. 14B, another circuit configuration of the class AB amplifier, a class B amplifier, and the like can be employed so long as the amplifier can be used for the output circuit of the operation amplifier, and a similar effect can be attained.

In addition, in FIGS. 14A and 14B, the transistor used in the operation amplifier is described as a MOS transistor, but the present invention is not limited to this. It is also possible to use a configuration in which bipolar transistors, FETs, and the like are entirely or partially used.

In addition to the CMUT, the piezoelectric element (PZT), the polymer molecule film (PVDF), or the like that outputs the voltage signal corresponding to the received ultrasonic wave at the time of the reception of the ultrasonic wave can also be used for the transducer according to the exemplary embodiment of the present invention. In a case where the voltage output type transducer is used, up to now, a configuration of arranging a voltage amplification type preamplifier (voltage amplification circuit) in the ultrasonic image forming system where the ultrasonic probe is connected is generally adopted. However, to reduce the signal degradation caused by a cable or the like extending from the probe to the system, it is also possible to use a configuration in which a voltage amplification type circuit (preamplifier) is arranged to be close to the transducer in the probe.

According to the present exemplary embodiment, it is possible to arrange the detection circuit (voltage amplification type preamplifier) of the voltage output type transducer in the probe in this manner. Thus, the power consumption in the detection circuit can be suppressed, and it is also possible to suppress the heat generation. On the other hand, since the voltage amplification type transducer has a low conversion efficiency of the elements when the transducer is used for the transmission of the ultrasonic wave, large heat generation occurs from the transducer. For that reason, even in a case where the transmission and reception are conducted, it is possible to provide the ultrasonic probe in which the ultrasonic wave can be received at a high accuracy and also the heat generation increase caused by the reception is suppressed by using the above-described configuration.

The probe according to the exemplary embodiment of the present invention may not use all of the elements 8 in a case where the acoustic wave reception or transmission is carried out once. For example, in case of the probe that performs the transmission of the ultrasonic wave, electronic scanning can be conducted while the driven elements are switched on the side of the apparatus to which the probe is connected. To elaborate, the ultrasonic wave transmission (that is, transmission beam forming) may be conducted once by using m pieces of the elements 8 among n pieces of the elements 8 provided in the transducer (m and n are positive integers, and m<n is established). In case of linier electronic scanning, while the elements 8 are switched sequentially at a next timing, the transmission beam forming may be conducted in units of m pieces of the elements 8. At that time, with regard to the elements 8 other than those selected to be used for the transmission and reception on the apparatus side, the detection circuit corresponding to the element may reduce the detection operation. For that reason, by using the embodiment of the present invention, the number of the detection circuits corresponding to the number of all the elements 8 provided in the transducer are arranged, only the detection circuit corresponding to the used element is operated, so that it is possible to suppress the power consumption to a minimum even when the electronic scanning is conducted.

Second Exemplary Embodiment

Figure 2A:
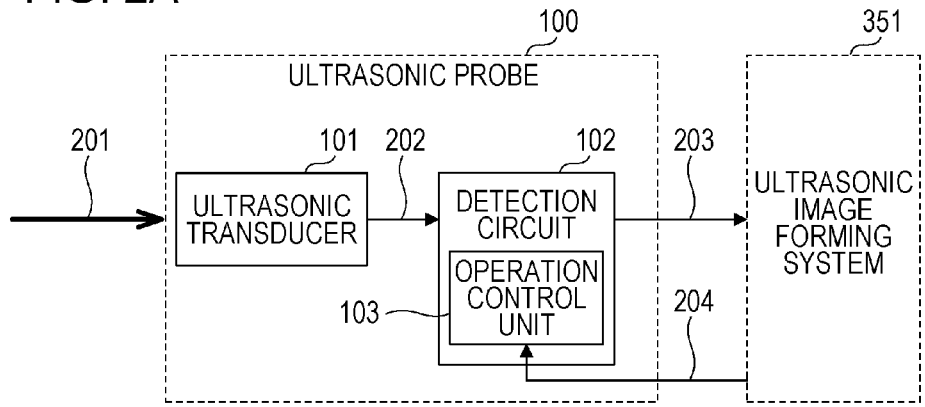
FIGS. 2A to 2D are explanatory diagrams for describing the detection circuit and the ultrasonic probe according to a second exemplary embodiment.
Figure 2B:
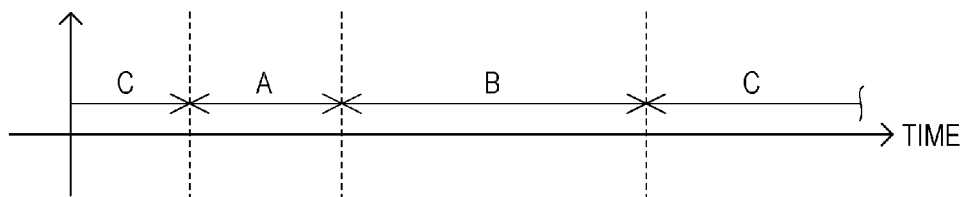
Figure 2C:
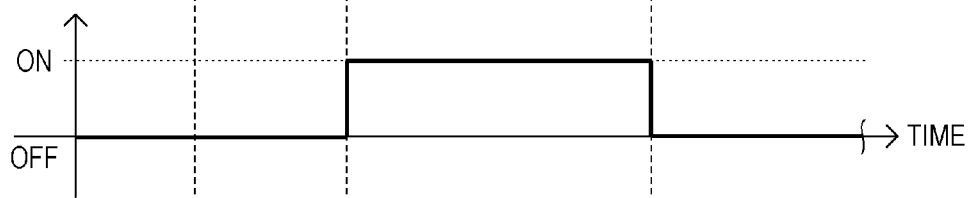
Figure 2D:
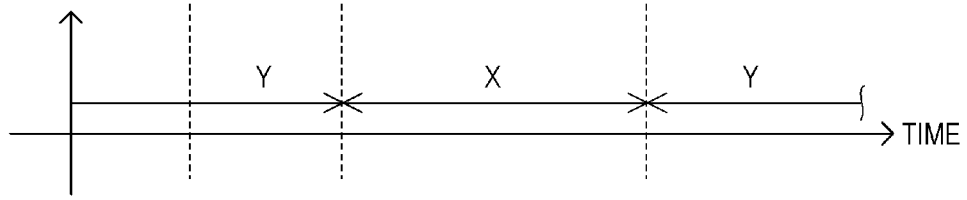

Next, a description will be given of a second exemplary embodiment by using FIG. 2. A difference of the second exemplary embodiment from the first exemplary embodiment resides in that the detection circuit includes the detection circuit operation control unit 103. The other configuration is the same as the first exemplary embodiment. According to the present exemplary embodiment, the detection circuit operation control unit 103 causes the detection circuit to operate or not to operate on the basis of a reception period signal. FIG. 2A is an explanatory diagram for describing the configurations of the detection circuit 102 and the ultrasonic probe 100 according to the present exemplary embodiment. In FIG. 2A, the detection circuit operation control unit 103, and an operation signal 204. FIGS. 2B, 2C, and 2D are explanatory diagrams for describing operations conducted by the detection circuit 102 and the ultrasonic probe 100. FIG. 2B represents a period for each operation mode of the ultrasonic probe 100. FIG. 2C represents the operation signal 204 of the ultrasonic probe 100. FIG. 2D represents an operation period of the detection circuit 102 of the ultrasonic probe 100. Each of the horizontal axes represents time.

The detection circuit 102 according to the present exemplary embodiment includes the detection circuit operation control unit 103 such as a switch for performing a control on the operation by the detection circuit. When the operation signal 204 representing the acoustic wave reception period is input (ON), the detection circuit operation control unit 103 sets the detection circuit 102 in a state where the detection operation is conducted (in a state during the period X). On the other hand, when the operation signal 204 represents a period other than the acoustic wave reception period (in a state of an OFF period), the detection circuit operation control unit 103 sets the detection circuit 102 in a state (Y) where the detection operation is not conducted. According to the present exemplary embodiment, the operation signal 204 is supplied from an ultrasonic image forming system 351 from an external part of the ultrasonic probe 100. The ultrasonic image forming system 351 controls a period during which the ultrasonic wave is generated and grasps a period during which the ultrasonic wave thereafter reaches the transducer 101. Thus, the ultrasonic image forming system 351 generates the operation signal 204 while the period during which the reception period the ultrasonic wave reaches the transducer 101 as the reception period. Since the detection circuit 102 is operated on the basis of the operation signal 204 from the ultrasonic image forming system 351, the detection circuit 102 can be operated only in the period during which the reception operation is to be conducted. It is therefore possible to suppress the power consumption in the detection circuit 102 to a requisite minimum. In this manner, according to the present exemplary embodiment, since the detection circuit 102 includes the detection circuit operation control unit 103, it is possible to easily realize the state where the detection circuit 102 is operated only during the reception period on the basis of the operation signal 204. As described above, according to the present exemplary embodiment, it is possible to easily realize the configuration of the probe that reduces the heat generation from the detection circuit without imparting the influence on the reception operation. With this configuration, the ultrasonic probe 100 in which the temperature increase hardly occurs can be easily provided.

Third Exemplary Embodiment

Figure 3A:
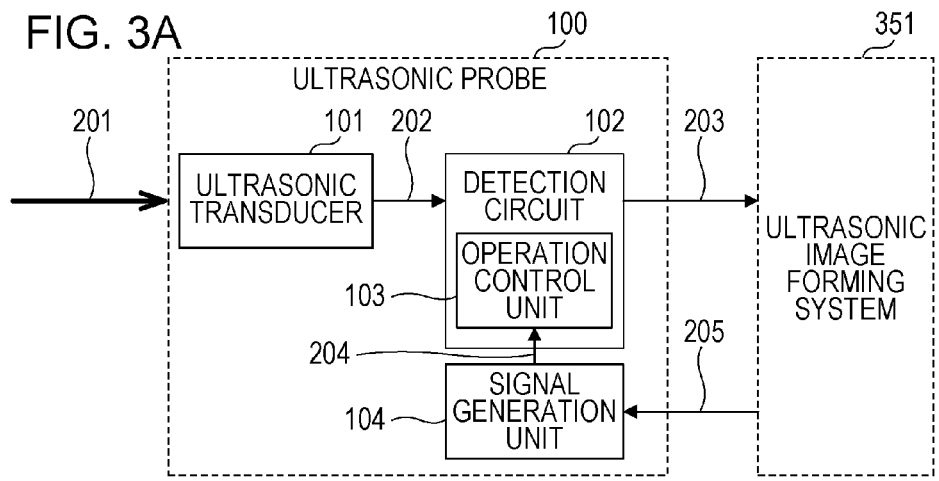
FIGS. 3A to 3F are explanatory diagrams for describing a third exemplary embodiment.

Next, a description will be given of a third exemplary embodiment by using FIGS. 3A to 3F. A difference of the third exemplary embodiment from the second exemplary embodiment resides in that an operation signal generation unit (hereinafter, which may also be referred to as signal generation unit) 104 configured to generate an operation signal. The other configuration is the same as the second exemplary embodiment. According to the present exemplary embodiment, the detection circuit 102 is caused to operate or not to operate by the operation signal 204 generated by the signal generation unit 104 in the ultrasonic probe 100. FIG. 3A is an explanatory diagram for describing configurations of the detection circuit 102 and the ultrasonic probe 100 according to the present exemplary embodiment. In FIG. 3A, the signal generation unit 104 such as a comparator or the like configured to control the switch and an ultrasonic wave generation signal 205 are illustrated.

Figure 3B:
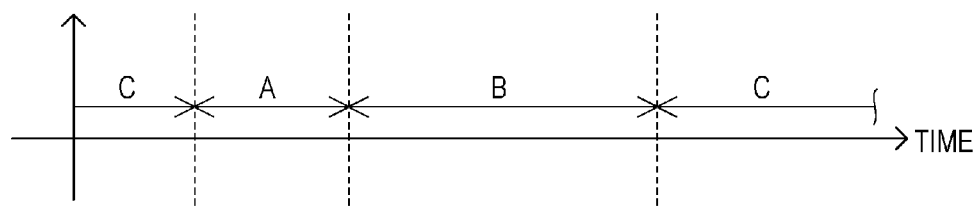
Figure 3C:
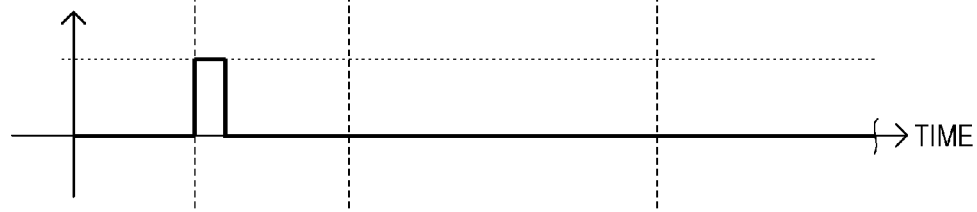
Figure 3D:
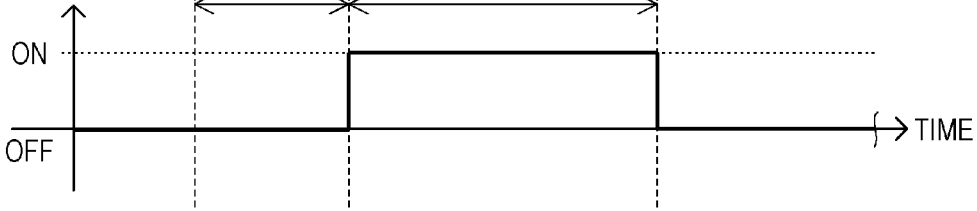
Figure 3E:
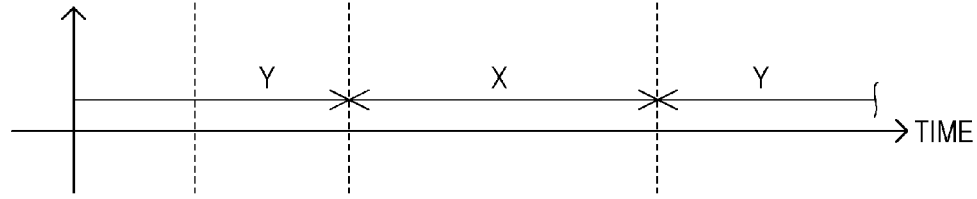

FIGS. 3B, 3C, 3D, and 3E are explanatory diagrams for describing operations conducted by the detection circuit 102 and the ultrasonic probe 100 according to the present exemplary embodiment. FIG. 3B represents a period for each operation mode of the ultrasonic probe 100. FIG. 3C represents the ultrasonic wave generation signal 205 of the ultrasonic probe 100. FIG. 2D represents the operation signal 204 of the ultrasonic probe 100. FIG. 3E represents an operation period of the detection circuit 102 of the ultrasonic probe 100. Each of the horizontal axes represents time.

The signal generation unit 104 according to the present exemplary embodiment generates the operation signal 204 on the basis of the ultrasonic wave generation signal 205. To elaborate, the detection operation of the detection circuit 102 is controlled on the basis of the transmission of the ultrasonic wave timing. Specifically, the signal generation unit 104 normally outputs the operation signal that does not represent the reception operation (OFF). When the ultrasonic wave generation signal 205 is input, after an elapse of a certain period TD1 since the ultrasonic wave generation signal 205 is input, the operation signal is switched to the operation signal that represents the reception operation (ON), and after a further elapse of a certain period TD2, the operation signal 204 is restored to the operation signal that does not represent the reception operation (OFF). The detection circuit 102 is caused to operate only during the acoustic wave reception period on the basis of the operation signal 204 generated by the signal generation unit 104.

According to the present exemplary embodiment, since the ultrasonic probe 100 includes the signal generation unit 104, the ultrasonic wave generation timing from the external part is received as the ultrasonic wave generation signal 205, and it is possible to optimally set the reception operation period. To elaborate, the detection circuit 102 is controlled so as not to perform the detection operation for a predetermined period after the transmission of the ultrasonic wave. For that reason, the detection circuit 102 is typically operated only during the acoustic wave reception period by simply inputting the ultrasonic wave generation signal 205 to the probe, and the power consumption in the detection circuit 102 can be suppressed.

Figure 3F:
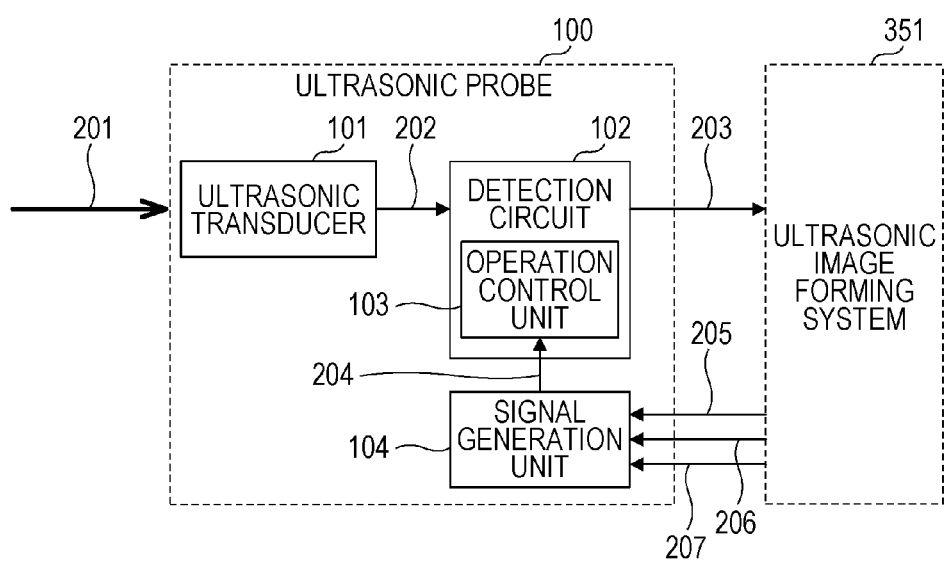

In the above explanation, only the ultrasonic wave generation signal 205 is input to the ultrasonic probe 100, but the present exemplary embodiment is not limited to this mode. As illustrated in FIG. 3F, it is also possible to adopt a configuration in which the ultrasonic wave reach delay information 206 representing the period TD1 and ultrasonic wave reception period information 207 representing the period TD2 are input to the ultrasonic probe 100, and the signal generation unit 104 generates the operation signal 204 on the basis of those information. According to this, even in a case where the measurement condition for the object to be measured is changed, the reception period of the ultrasonic probe 100 can be changed to an optimal reception period. Therefore, the power consumption in the detection circuit 102 can be suppressed to the minimum for every measurement condition. It is thus possible to provide the ultrasonic probe 100 in which the reception period to be used is secured even when the measurement condition is changed, and also the heat generation amount is suppressed to the minimum.

Fourth Exemplary Embodiment

Figure 4A:
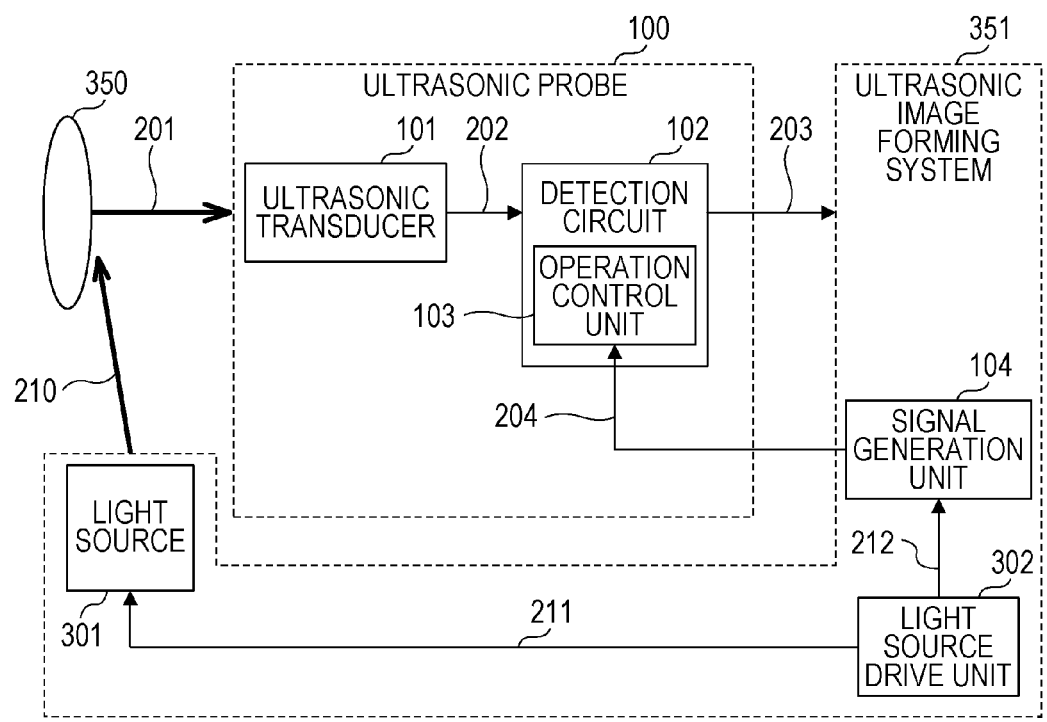
FIGS. 4A to 4G are explanatory diagrams for describing a fourth exemplary embodiment.
Figure 4B:
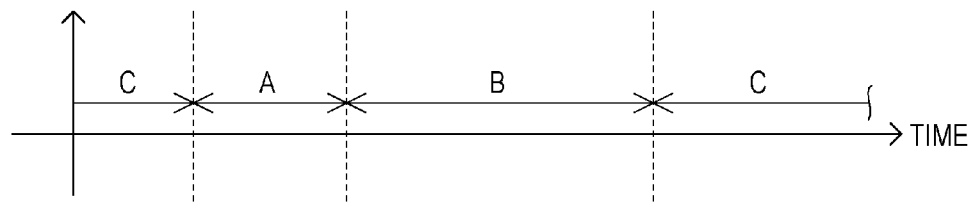
Figure 4C:
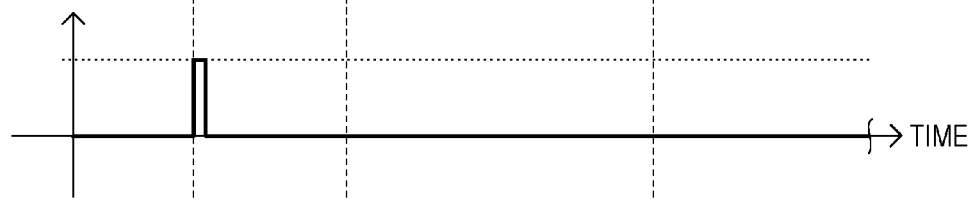
Figure 4D:
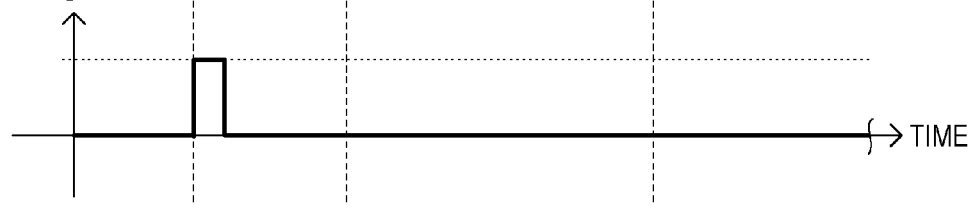
Figure 4E:
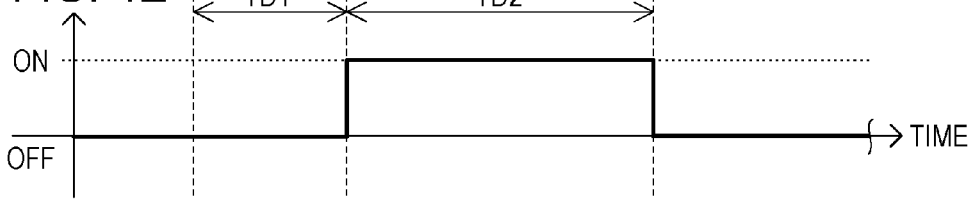
Figure 4F:
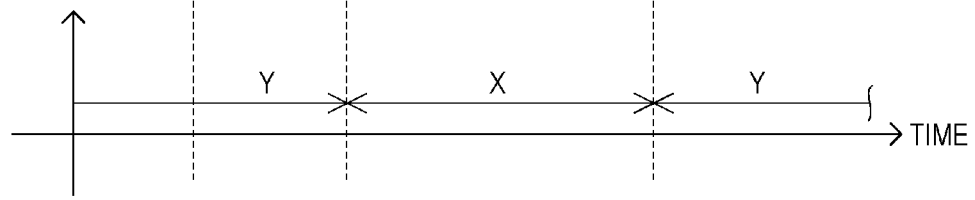

Next, a description will be given of a fourth exemplary embodiment by using FIGS. 4A to 4F. A difference of the fourth exemplary embodiment from the other exemplary embodiments resides in that a photo-acoustic effect is used for the ultrasonic wave generation unit. The other configuration is the same as the second and third exemplary embodiments. According to the present exemplary embodiment, the object is irradiated with light, and an ultrasonic wave (hereinafter, which may also be referred to as photoacoustic wave) generated from the object is received. FIG. 4A is an explanatory diagram for describing the configurations of the detection circuit and the ultrasonic probe 100 according to the present exemplary embodiment. In FIG. 4A, a light source 301 and a light source drive unit 302 are illustrated. FIGS. 4B, 4C, 4D, 4E, and 4F are explanatory diagrams for describing operations conducted by the detection circuit 102, the ultrasonic probe 100, and the like according to the present exemplary embodiment. FIG. 4B represents a period for each operation mode of the ultrasonic probe 100. FIG. 4C represents a light source drive signal 211 of the ultrasonic probe 100. FIG. 4D represents a light source drive synchronization signal 212 of the ultrasonic probe 100. FIG. 4E represents the operation signal 204 of the ultrasonic probe 100. FIG. 4F represents an operation period of the detection circuit 102 of the ultrasonic probe 100. Each of the horizontal axes represents time.

The object 350 is irradiated with light 210 generated when the light source 301 is driven by the light source drive unit 302, and the ultrasonic wave is generated by the photoacoustic effect in the object. Since the transducer 101 receives the generated ultrasonic wave 201, a shape and a position of a measurement subject 350 are detected on the basis of the received signal. Here, the light source drive unit 302 outputs the light source drive signal 211 and the light source drive synchronization signal 212 in synchronization with the light source drive signal 211. According to the present exemplary embodiment, the signal generation unit 104 generates the operation signal 204 on the basis of the light source drive synchronization signal 212. To elaborate, the detection operation of the detection circuit 102 is controlled on the basis of a light emitting timing. As described above, the operation signal 204 is generated on the basis of the light emitting timing for the light that excites the photoacoustic wave in the detection circuit 102 used for the transducer 101 that receives the photoacoustic wave generated by the photo-acoustic effect. The detection circuit operation control unit 103 then performs an ON/OFF control of the detection operation on the basis of this operation signal. To elaborate, the detection circuit 102 is controlled so as not to conduct the detection operation for a predetermined period from the light generation. With this configuration, it is possible to perform the detection operation using the detection circuit 102 in accordance with the light emission from the light source, and it is also possible to suppress the power consumption in the detection circuit 102. In the ultrasonic image forming system using the photo-acoustic effect, by using the present exemplary embodiment, it is possible to provide the ultrasonic probe 100 in which the heat generation from the detection circuit is suppressed. According to the present exemplary embodiment, the configuration in which the signal generation unit 104 is arranged in the ultrasonic image forming system 351 has been described, but the signal generation unit 104 may be arranged in the ultrasonic probe 100.

Figure 4G:
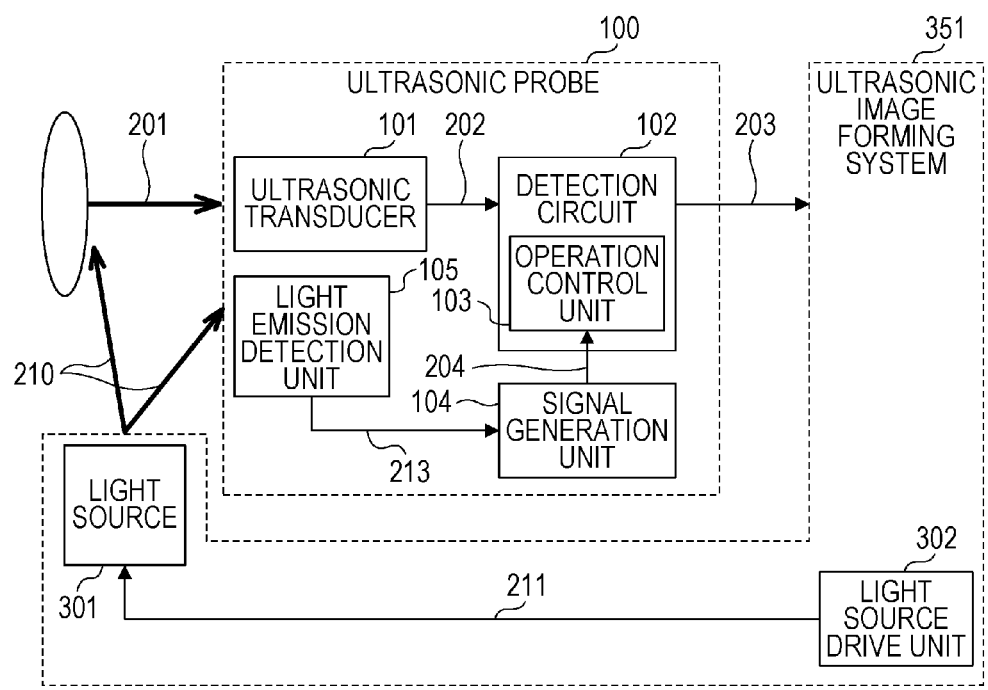

A modified mode of the present exemplary embodiment will be described by using FIG. 4G. In FIG. 4G, a light emission detection unit 105 is illustrated. A difference of the present modified mode from the mode of FIG. 4A in that the light emission detection unit 105 configured to detect the light emission of the light source 301 is provided. The light emission detection unit 105 detects the light 210 emitted from the light source 301 and generates a light emission detection signal 213. The velocity of light is extremely high, and a delay hardly exists from the light emitting timing for the light. The light emission detection unit 105 accurately detects the light emitting timing of the light source, and it is possible to generate the light emission detection signal 213. The signal generation unit 104 generates the operation signal 204 on the basis of the light emission detection signal 213, and the detection circuit 102 performs the operation on the basis of the operation signal 204. By using the present modified mode, even when the drive information from the light source drive unit 302 does not exist in the ultrasonic image forming system using the photo-acoustic effect, it is possible to provide the ultrasonic probe 100 in which the heat generation from the detection circuit is suppressed.

Fifth Exemplary Embodiment

Figure 5A:
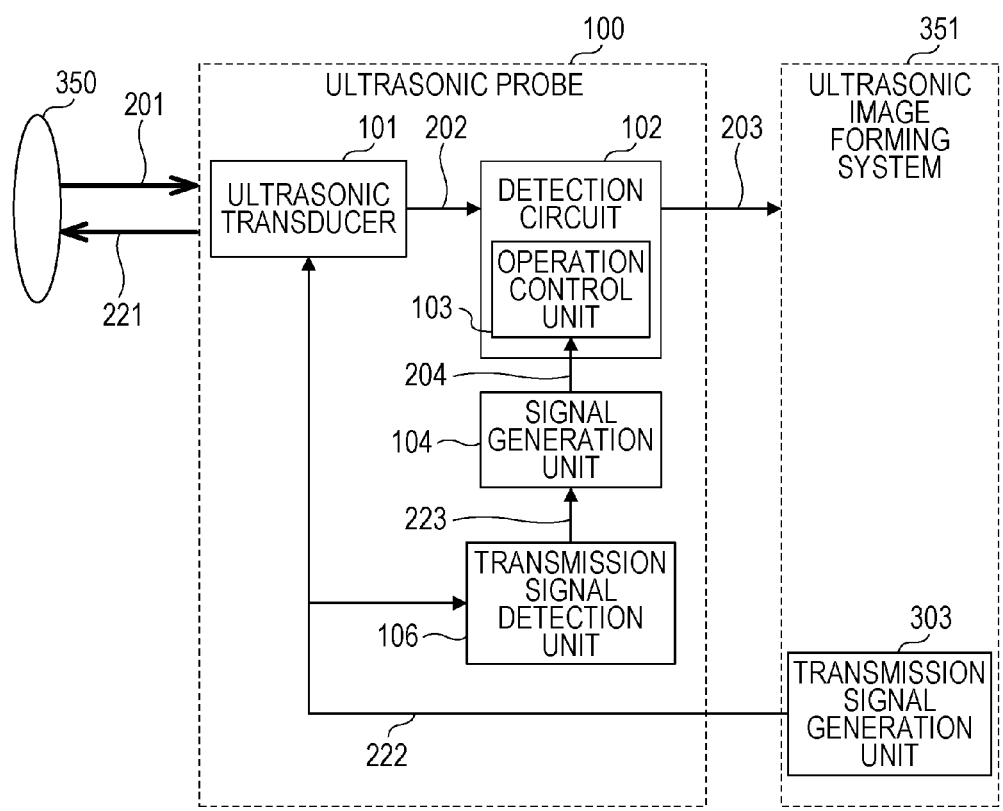
FIGS. 5A to 5F are explanatory diagrams for describing a fifth exemplary embodiment.
Figure 5B:
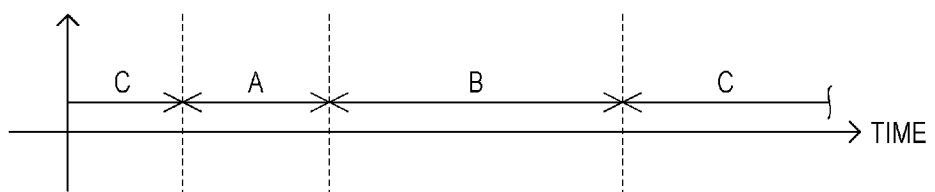
Figure 5C:
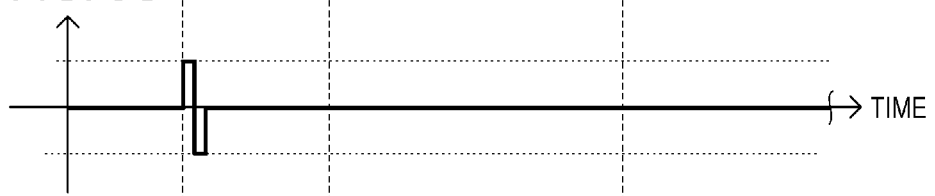
Figure 5D:
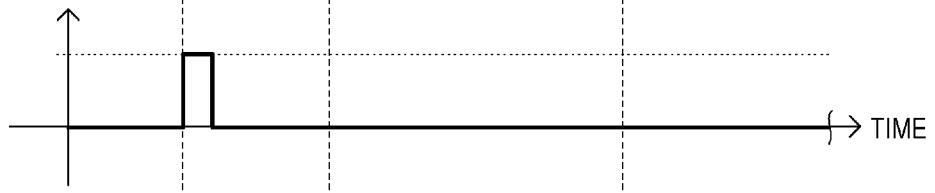
Figure 5E:
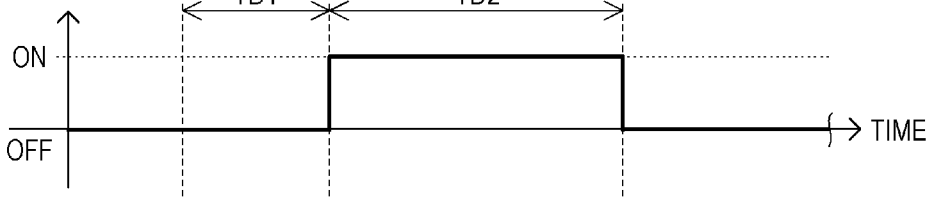
Figure 5F:
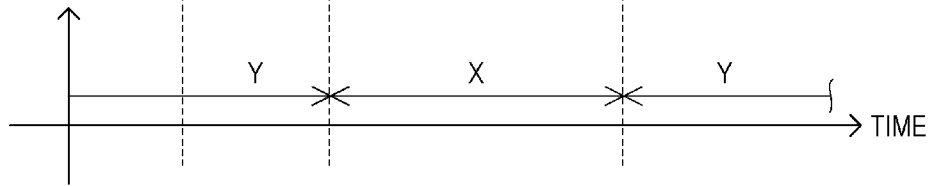

Next, a description will be given of a fifth exemplary embodiment by using FIGS. 5A to 5F. A difference of the fifth exemplary embodiment from the other exemplary embodiments resides in that a transmission signal detection unit is provided. The other configuration is the same as the third exemplary embodiment. To elaborate, according to the present exemplary embodiment, the transmission voltage signal (transmission signal) applied to the transducer 101 is detected to obtain the transmission of the ultrasonic wave timing, and the operation signal 204 is generated on the basis of the information. FIG. 5A is an explanatory diagram for describing the configurations of the detection circuit 102 and the ultrasonic probe 100 according to the present exemplary embodiment. In FIG. 5A, a transmission signal detection unit 106, a transmission ultrasonic wave 221, a transmission voltage signal (transmission signal) 222, a transmission detection signal 223, and a transmission signal generation unit 303 are illustrated. FIGS. 5B, 5C, 5D, 5E, and 5F are explanatory diagrams for describing operations conducted by the ultrasonic probe and the like according to the present exemplary embodiment. FIG. 5B represents a period for each operation mode of the ultrasonic probe 100. FIG. 5C represents the transmission voltage signal 222 of the ultrasonic probe 100. FIG. 5D represents the transmission detection signal 223 of the ultrasonic probe 100 according to the present exemplary embodiment. FIG. 5E represents the operation signal 204 of the ultrasonic probe 100. FIG. 5F represents an operation period of the detection circuit 102 of the ultrasonic probe 100. Each of the horizontal axes represents time.

The transmission voltage signal 222 is generated in the transmission signal generation unit 303 and applied to the transducer 101. The transducer 101 generates vibration by the transmission voltage signal 222 and transmits the ultrasonic wave 221. When the transmission ultrasonic wave 221 reaches the object 350 after a certain time, the transmission ultrasonic wave 221 is reflected there. After a certain time, the transmission ultrasonic wave 221 returns to the transducer 101 as the reception ultrasonic wave 201. The transducer 101 detects (receives) a vibration change generated by the returned reception ultrasonic wave 201 in the detection circuit 102. According to the present exemplary embodiment, the transmission voltage signal 222 is applied to the transducer 101 and also input to the transmission signal detection unit 106 at the same time. When the transmission voltage signal 222 has a voltage higher than or equal to a certain voltage in the transmission signal detection unit 106, the transmission detection signal 223 is generated. This function can easily be realized by using a comparator or the like. The generated transmission detection signal 223 is input to the signal generation unit 104. In the signal generation unit 104, after an elapse of the period TD1 after the input of the transmission detection signal 223, the operation signal 204 is set as the signal (ON) that represents the reception operation. To elaborate, the detection circuit 102 is controlled so as not to perform the detection operation for a predetermined period after the transmission of the ultrasonic wave. After a further elapse of the period TD2, the operation signal 204 is output as the signal (OFF) that does not represent the reception operation.

In the above-described manner, according to the present exemplary embodiment, the operation signal generation unit 104 generates an operation signal on the basis of the transmission signal for the transducer 101 to generate the acoustic wave. The detection circuit operation control unit 103 then performs the ON/OFF control of the detection operation on the basis of the operation signal 204 from the operation signal generation unit 104. Herein, the operation signal generation unit 104 includes the transmission signal detection unit 106 configured to detect the transmission voltage signal that is applied to the transducer 101 for generating the acoustic wave. The operation signal generation unit 104 subsequently detects the acoustic wave transmission operation in the transmission signal detection unit 106. The operation signal 204 is not output for a predetermined time after the acoustic wave transmission operation is detected, and the operation signal 204 is then output after an elapse of the predetermined time.

According to the present exemplary embodiment, the ultrasonic probe 100 includes the transmission signal detection unit 106. For that reason, the transmission of the ultrasonic wave timing can be detected by the transmission voltage signal 222 alone without another signal input, and it is possible to reduce the heat generation by controlling the operation of the detection circuit 102.

Sixth Exemplary Embodiment

Next, a description will be given of a sixth exemplary embodiment by using FIGS. 6A to 6F. A difference of the sixth exemplary embodiment from the other exemplary embodiments resides in that a protection switch 107 of the detection circuit is provided. The other configuration is the same as the fifth exemplary embodiment. According to the present exemplary embodiment, it is characterized in that the transmission voltage (transmission signal) is detected on the basis of switch disconnection information 224 of the protection switch 107 (which plays the same role as the transmission detection signal 223) of the detection circuit 102. In FIG. 6A, the protection switch 107 and the switch disconnection information 224 are illustrated. According to the present exemplary embodiment, the transmission voltage signal 222 is connected to the transducer 101 and also connected to the detection circuit 102 via the protection switch 107. When the transmission voltage signal 222 exceeds a certain voltage, the protection switch 107 detects the state and disconnects the connection to the detection circuit 102. According to this, it is possible to reduce the application of a high voltage to the detection circuit 102 and the damage of the detection circuit 102. On the other hand, since only a faint voltage is generated in the protection switch 107 during a period in which the transducer 101 receives the ultrasonic wave, the connection of the wiring to the detection circuit 102 remains. According to this, the detection signal 202 generated by the transducer 101 because of the reception of the ultrasonic wave is input to the detection circuit 102 via the protection switch 107 and changed into the detection output signal 203 to be output. FIGS. 6B to 6F are drawings similar to FIGS. 5B to 5F. In the above-described manner, when the transmission voltage signal applied to the transducer 101 is higher than or equal to a certain voltage, the transmission signal detection unit 106 detects the transmission voltage signal on the basis of switch disconnection information 224 of the protection switch 107 that disconnects the connection to the detection circuit 102 from the transducer 101.

According to the present exemplary embodiment, the disconnection information 224 of the protection switch 107 is input to the signal generation unit 104. When the transmission voltage signal 222 is applied to the transducer 101, the same voltage is also applied to the protection switch 107, so that the wiring of the protection switch 107 to the detection circuit 102 is disconnected. The state in which the transmission voltage signal 222 is applied to the transducer 101 can be detected by checking the disconnection information 224 of the protection switch 107, and it is possible to detect the timing at which the ultrasonic wave is transmitted. The disconnection information 224 is input to the signal generation unit 104, and the operation signal 204 is generated on the basis of the disconnection information 224. As described above, according to the present exemplary embodiment, the protection switch 107 functions as the transmission signal detection unit 106.

According to the present exemplary embodiment, since the protection switch 107 provided in the ultrasonic probe 100 has the function of the transmission signal detection unit 106, the transmission voltage signal can be detected without an addition of a constitution element, and it is possible to reduce the heat generation by controlling the operation of the detection circuit 102.

Seventh Exemplary Embodiment

Next, a description will be given of a seventh exemplary embodiment by using FIGS. 7A to 7D. A difference of the seventh exemplary embodiment from the other exemplary embodiments resides in the control method for the operation of the detection circuit. The other configuration is the same as the first to sixth exemplary embodiments. According to the present exemplary embodiment, it is characterized in that the operation of the detection circuit 102 is controlled by a voltage supply to the detection circuit 102.

In FIGS. 7A to 7D, a supply unit 108, a voltage amplification unit 110 of the detection circuit 102, and the output unit 112 of the detection circuit 102 are illustrated. According to the present exemplary embodiment, the detection circuit operation control unit 103 functions as the supply unit 108 of a bias voltage. The operation signal 204 is input to the supply unit 108. In a case where the operation signal 204 represents the reception operation, at least one of the voltage amplification unit 110 and the output unit 112 in the detection circuit 102 is supplied with a bias voltage 113 in the supply unit 108. On the other hand, in a case where the operation signal 204 does not represent the reception operation, the supply of the bias voltage 113 to at least one of the voltage amplification unit 110 and the output unit 112 in the detection circuit 102 is stopped. In the above-described manner, according to the present exemplary embodiment, the detection circuit operation control unit 103 supplies a predetermined voltage to the power supply of the detection circuit 102 when the operation signal 204 indicates the reception period, and the detection circuit operation control unit 103 does not supply the predetermined voltage to the power supply of the detection circuit 102 when the operation signal 204 does not indicate the reception period. According to the present exemplary embodiment, the operation of the detection circuit 102 is controlled by the voltage supply to the constitution element of the detection circuit 102, so that it is possible to operate the detection circuit 102 reliably only during the reception period by using the simple configuration. For that reason, it is possible to provide the compact ultrasonic probe with the low heat generation in which the plurality of detection circuits can easily be controlled.

Figure 7A:
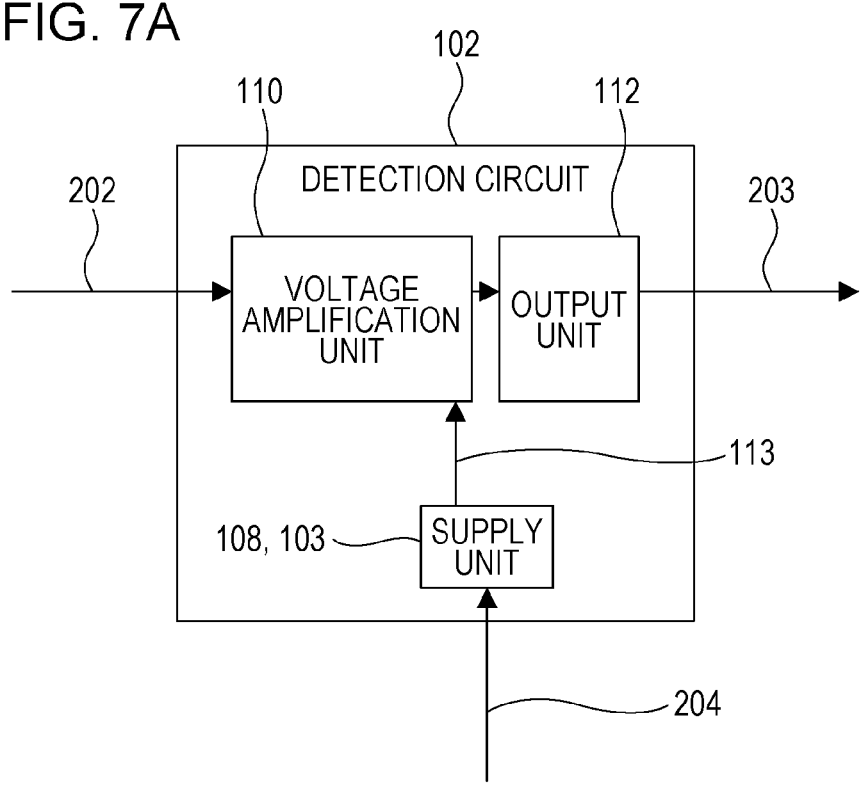
FIGS. 7A to 7D are explanatory diagrams for describing the detection circuit and the ultrasonic probe according to a seventh exemplary embodiment.
Figure 7B:
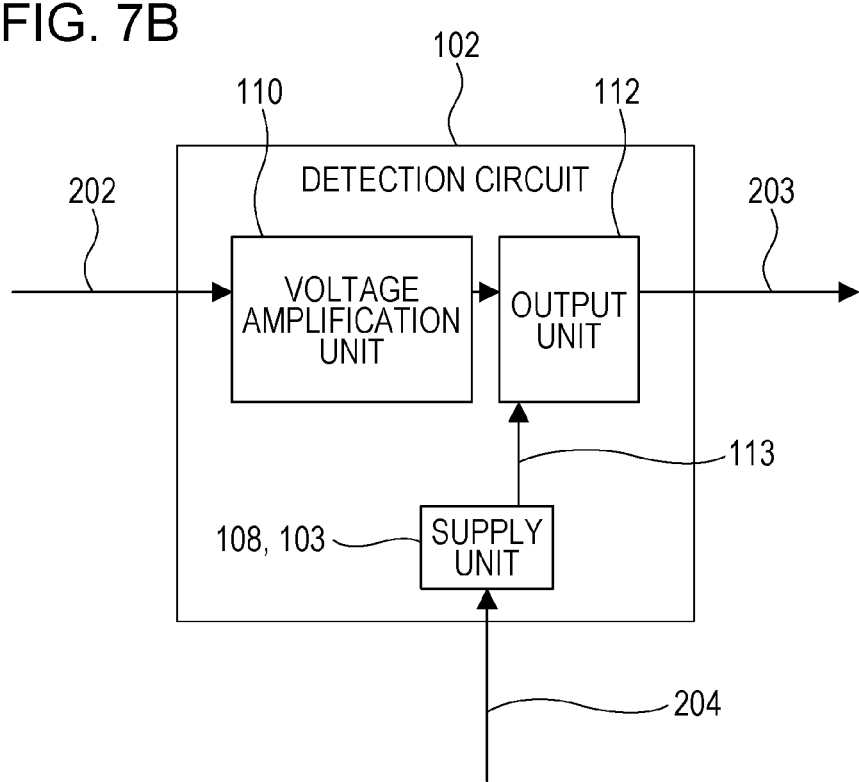
Figure 7C:
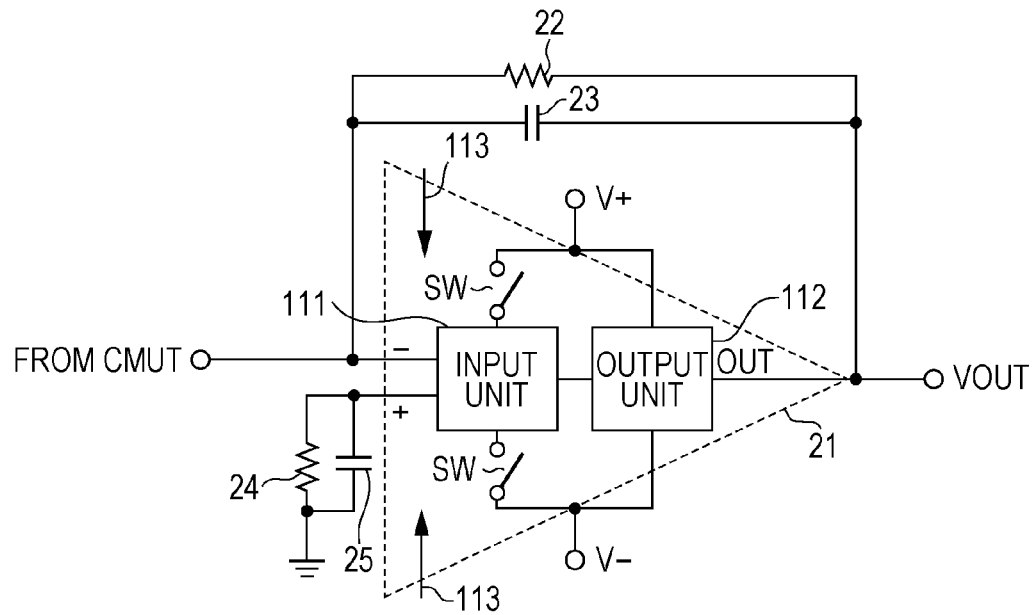

In addition, according to the present exemplary embodiment, the present invention is not limited to the above-described configuration, and as illustrated in FIG. 7C, it is also possible to adopt a configuration of controlling the supply of the bias voltage 113 to the input unit 111 of the transimpedance circuit in the current-voltage conversion circuit. Since a high bias current flows through the input unit 111 of the transimpedance circuit to reduce noise, when the bias current stops, the power consumption can significantly be reduced. Therefore, with the adoption of this mode, it is possible to effectively reduce the power consumption particularly in the configuration of using the high-speed transimpedance circuit where the detection circuit is to be used to detect the capacitative CMUT at a high accuracy.

Figure 7D:
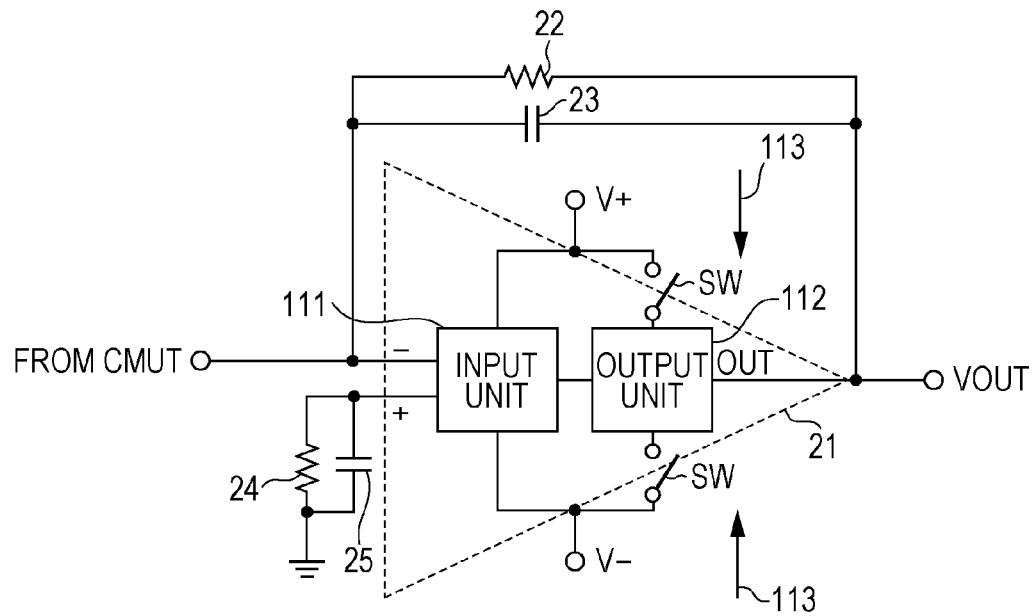

In addition, as illustrated in FIG. 7D, a configuration of controlling the supply of the bias voltage 113 to the output unit 112 of the transimpedance circuit in the current-voltage conversion circuit can be adopted and also be used in combination with the configuration illustrated in the FIG. 7C. According to this, the power consumption of the detection circuit can further be suppressed.

Eighth Exemplary Embodiment

Next, a description will be given of an eighth exemplary embodiment by using FIGS. 8A to 8D. A difference of the eighth exemplary embodiment from the other exemplary embodiments resides in the control method for the operation of the detection circuit 102. The other configuration is the same as the first to the sixth exemplary embodiments. According to the present exemplary embodiment, a supply unit for bias current used for the voltage amplification unit 110 and the output unit 112 of the detection circuit 102 to operate is arranged at an external part of the voltage amplification unit 110 and the output unit 112 in the detection circuit 102. It is characterized in that the presence and the absence of the bias current supply to the detection circuit 102 are switched by a bias current supply unit 109 arranged at the external part of the detection circuit 102 to control the operation of the detection circuit 102.

Figure 8A:
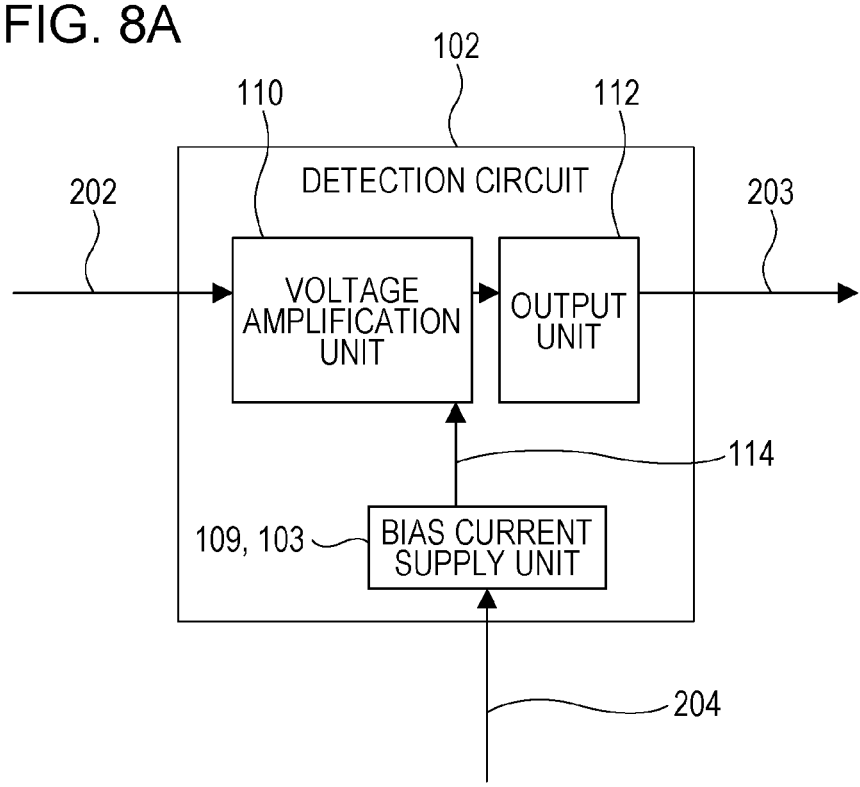
FIGS. 8A to 8D are explanatory diagrams for describing the detection circuit and the ultrasonic probe according to an eighth exemplary embodiment.

In FIG. 8A, the bias current supply unit 109, the voltage amplification unit 110 and the output unit 112 in the detection circuit 102 are illustrated. According to the present exemplary embodiment, the detection circuit operation control unit 103 for the detection circuit 102 is the bias current supply unit 109. The operation signal 204 is input to the bias current supply unit 109. In a case where the operation signal 204 represents the reception operation in the bias current supply unit 109, a connected part within the detection circuit 102 is supplied with a bias current 114. In a case where the operation signal 204 does not represent the reception operation, the supply of the bias current 114 to the connected part within the detection circuit 102 is stopped.

In FIG. 8A, the bias current supply unit 109 is connected to a bias current terminal of the voltage amplification unit 110 of the detection circuit 102. The voltage amplification unit 110 performs a voltage amplification operation while a predetermined current flows through this bias current terminal. For that reason, the voltage amplification operation is not carried out if the current does not flow through this bias current terminal. In this manner, the voltage amplification operation of the detection circuit 102 can be controlled into an arbitrary state by using the present exemplary embodiment, and it is possible to reduce the power consumption. It suffices if this bias current supply unit controls the current supply, so that the bias current supply unit can simply be realized by using a compact switch. The wirings and switches are used by almost the same order as the detection circuits, but the entire circuit can be composed of an integrated circuit, and the circuit area can significantly be reduced by the integration. In this manner, according to the present exemplary embodiment, since the bias current supply unit 109 is provided, the operation of the detection circuit 102 can easily be controlled by the presence or absence of the current supply. For that reason, it is possible to provide the ultrasonic probe having the small circuit area while the circuit is integrated, and also the power consumption is reduced.

Figure 8B:
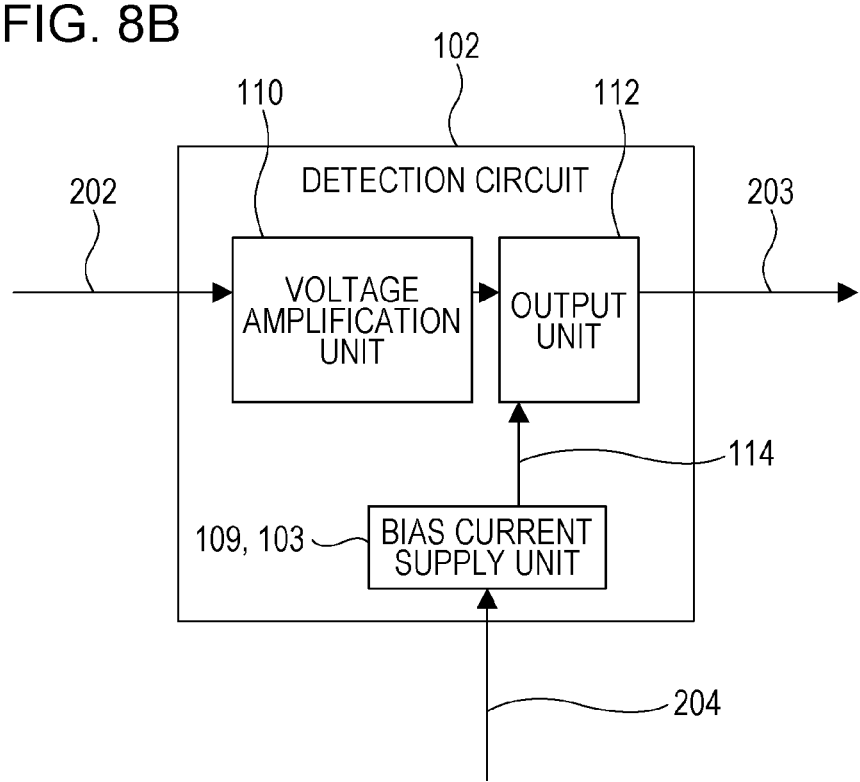

In addition, as in FIG. 8B, a configuration of controlling the supply of the bias current 114 to the output unit 112 of the detection circuit 102 can be adopted and also be used in combination with the configuration illustrated in FIG. 8A. Moreover, as in the configuration of FIG. 8B, a configuration of simultaneously control the bias current 114 to the voltage amplification unit 110 as the input unit and the bias current 114 to the output unit 112 can also be adopted. In the above-described manner, according to the exemplary embodiment of FIGS. 8A to 8D, the detection circuit operation control unit 103 supplies the bias current to the detection circuit 102 when the operation signal indicates the acoustic wave reception period. On the other hand, when the operation signal does not indicate the acoustic wave reception period, the bias current is not supplied to the voltage amplification unit of the detection circuit 102 or the output unit.

In a case where the wiring length from the probe to the system is long (the drive load in the cable is high), a current drive ability of the output unit is set to be high to transmit the signal. In accordance with that setting, the bias current value of the output unit is also set to have a high value. With the adoption of the above-described mode, it is possible to effectively reduce the power consumption even in the configuration of using the long output cable.

Figure 8C:
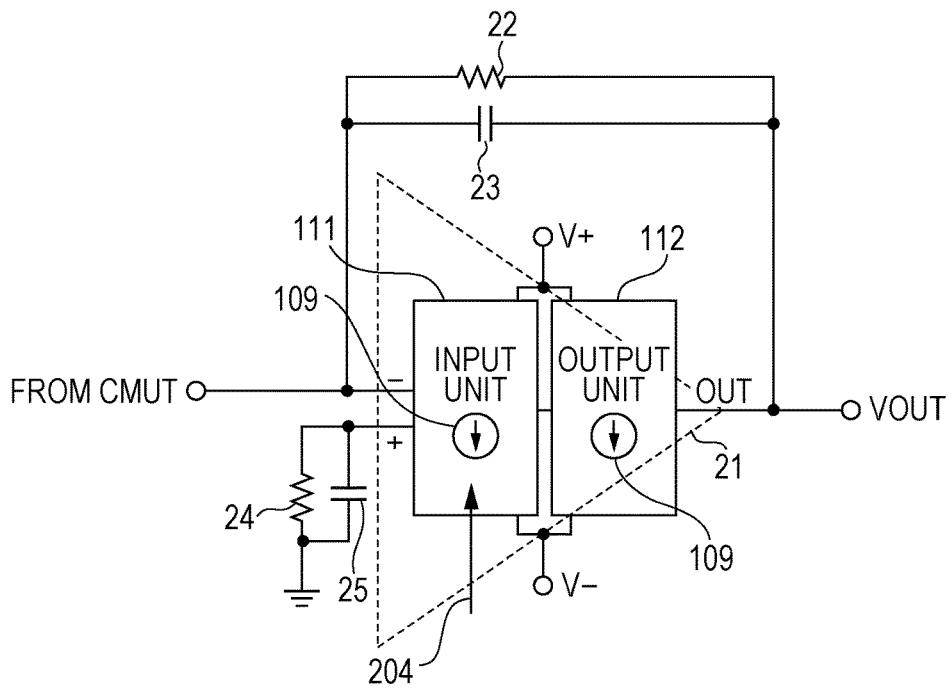

In addition, according to the present exemplary embodiment, the present invention is not limited to the above-described configuration, and as in FIG. 8C, a configuration of controlling the supply of the bias current 114 to the input unit 111 of the transimpedance circuit in the current-voltage conversion circuit can also be adopted. Since a high bias current flows through the input unit 111 of the transimpedance circuit to reduce noise, when the bias current stops, the power consumption can significantly be reduced. Therefore, with the adoption of this mode, it is possible to effectively reduce the power consumption particularly in the configuration of using the high-speed transimpedance circuit where the detection circuit is to be used to detect the capacitive CMUT at a high accuracy.

Figure 8D:
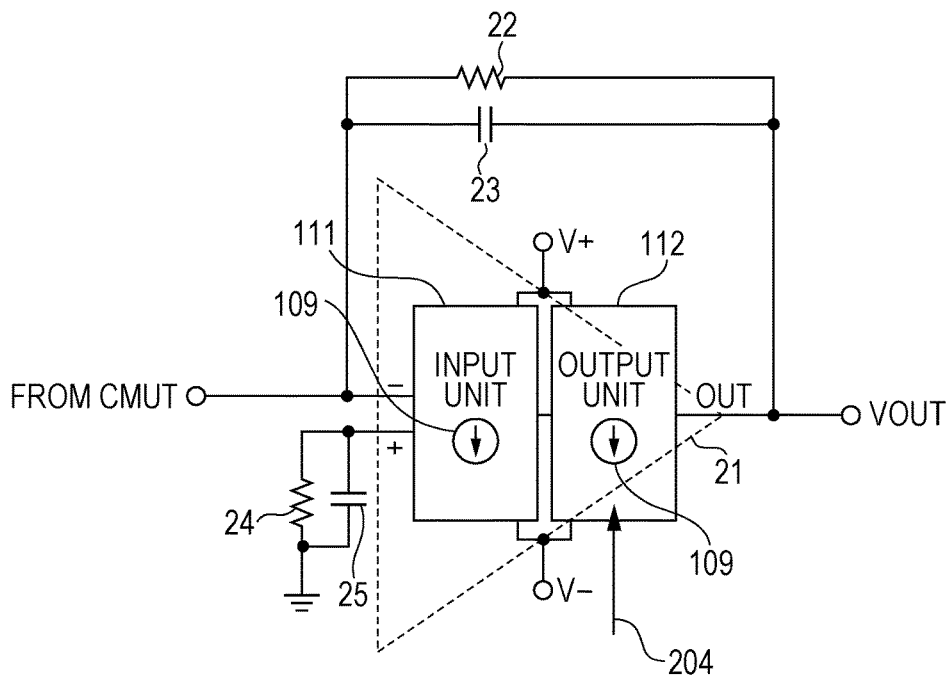

Moreover, like FIG. 8D, a configuration of controlling the supply of the bias current 114 to the output unit 112 of the transimpedance circuit in the current-voltage conversion circuit can be adopted and also be used in combination with the configuration illustrated in FIG. 8C. According to this, the power consumption of the detection circuit 102 can be further suppressed.

Ninth Exemplary Embodiment

The detection circuit, the transducer, and the like described in the above-described exemplary embodiments can be applied to the subject information acquiring apparatus using the acoustic wave. The transducer receives the acoustic wave from the subject, and subject information on which an optical characteristic value of the subject such as an optical-absorption coefficient is reflected, subject information on which a difference in acoustic impedances is reflected can be obtained by using the electric signal output via the detection circuit according to the exemplary embodiment of the present invention. The ultrasonic image forming system 351 according to the above-described exemplary embodiment corresponds to a processing unit of the present exemplary embodiment.

More specifically, the subject is irradiated with light (electromagnetic waves including visible rays or infrared rays) by at least one of the subject information acquiring apparatuses according to the present exemplary embodiment. With this configuration, the photoacoustic waves generated at plural positions (sites) in the subject are received, and a characteristic distribution indicating a distribution of characteristic information corresponding to each of the plural positions in the subject is obtained. The characteristic information obtained by way of the photoacoustic wave indicates characteristic information related to light absorption and includes characteristic information on which an initial sound pressure of the photoacoustic wave generated by the light irradiation or a light energy absorption density derived from the initial sound pressure, an absorption coefficient, a concentration of a material constituting a tissue, or the like is reflected. The concentration of the material includes, for example, an oxygen saturation, a total hemoglobin concentration, an oxyhemoglobin or deoxyhemoglobin concentration, or the like. The subject information acquiring apparatus may also be used for a diagnosis on a malignancy, a vascular disease, or the like of a human being or an animal, a wait-and-see approach of a chemical treatment, or the like. Therefore, it is supposed that the subject includes a living body, specifically, a diagnosis target such as a breast, a cervical region, or an abdominal region of the human being or the animal. A light absorber existing in the subject refers to a tissue where the absorption coefficient is relatively high in the subject. For example, when a part of the human body is the subject, the light absorber includes a blood vessel containing much of oxyhemoglobin, deoxyhemoglobin, or a combination of those, a tumor containing many newborn blood vessels, a plaque of the carotid wall, and the like. Furthermore, the light absorber includes a molecular probe specifically bound to the malignancy or the like by using gold particles, graphite, or the like, a capsule that transfers a medical agent, and the like.

A distribution related to an acoustic characteristic in the subject can also be obtained by not only receiving the reception of the photoacoustic wave but also receiving the reflected wave by the ultrasonic wave echo in which the ultrasonic wave transmitted from the probe including the transducer is reflected in the subject. This distribution related to the acoustic characteristic includes a distribution on which a difference in the acoustic impedances of the tissues inside the subject is reflected. It is however noted that the transmission and reception of the ultrasonic wave and the obtainment of the distribution related to the acoustic characteristic may be skipped.

Figure 12A:
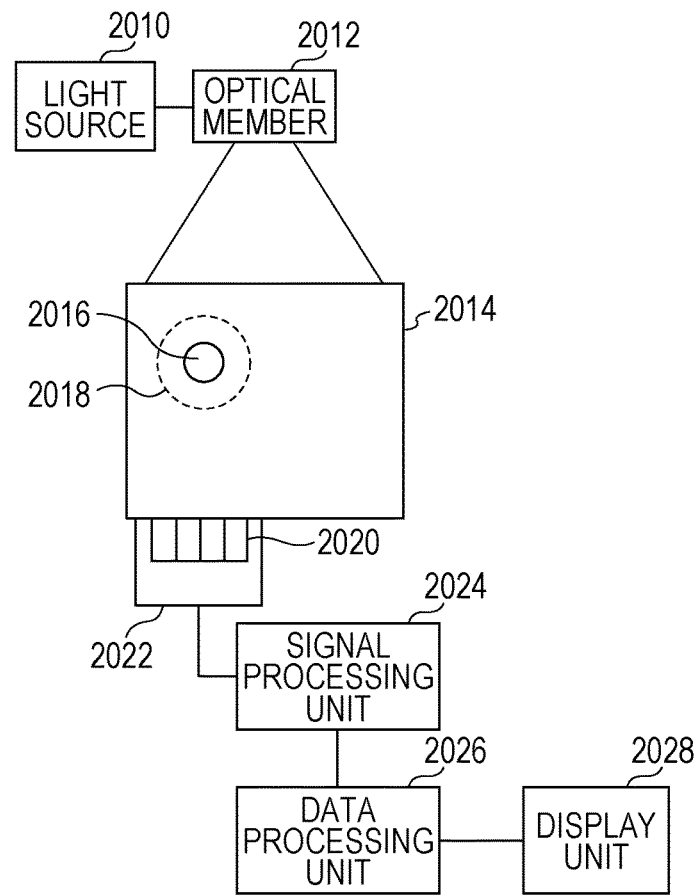
FIGS. 12A and 12B illustrate a subject information acquiring apparatus using the detection circuit according to an embodiment.

FIG. 12A illustrates the subject information acquiring apparatus using the photo-acoustic effect. A subject 2014 is irradiated with pulsed light emitted from a light source 2010 via an optical member 2012 such as a lens, a mirror, an optical fiber, or the like. A light absorber 2016 existing in the subject 2014 absorbs energy of the pulsed light and generates a photoacoustic wave 2018 corresponding to an acoustic wave. A transducer 2020 within a probe (searching probe) 2022 receives the photoacoustic wave 2018 to be transduced into an electric signal and outputs the electric signal to a signal processing unit 2024 via the detection circuit. The signal processing unit 2024 performs signal processing such as an A/D conversion or an amplification on the input electric signal and output the electric signal to a data processing unit 2026. The data processing unit 2026 uses the input signal and obtains the subject information (characteristic information on which the optical characteristic value of the subject such as the optical-absorption coefficient is reflected) as image data. Herein, the signal processing unit 2024 and the data processing unit 2026 are collectively referred to as processing unit. A display unit 2028 displays an image based on the image data input from the data processing unit 2026.

Figure 12B:
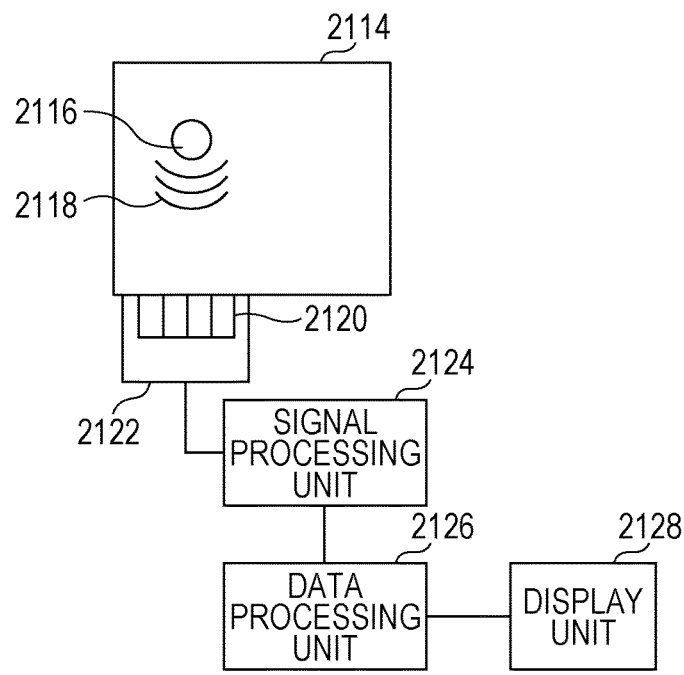
Figure 13:
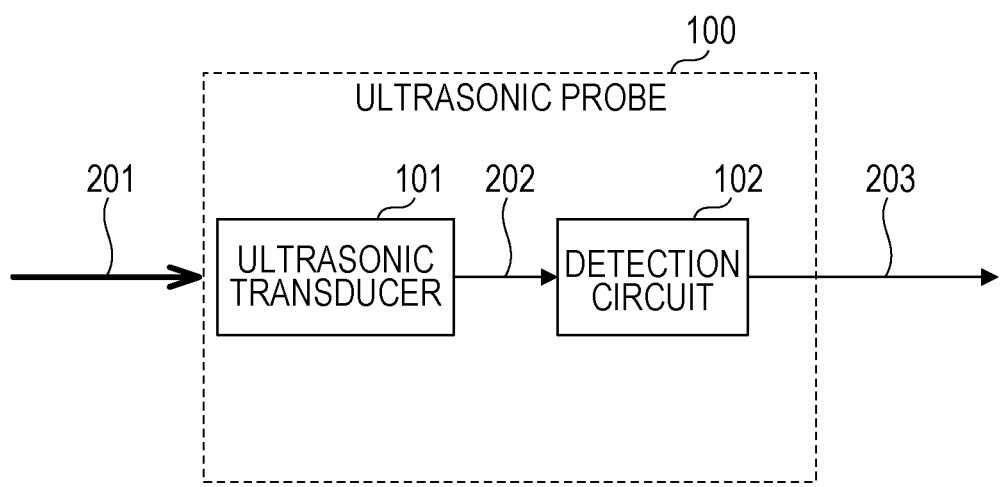
FIG. 13 is an explanatory diagram for describing an ultrasonic probe in related art.

FIG. 12B illustrates the subject information acquiring apparatus such as an ultrasonic wave echo diagnosis apparatus using the reflection of the acoustic wave (ultrasonic wave). The acoustic wave transmitted from a transducer 2120 within a probe (searching probe) 2122 to a subject 2114 is reflected by a reflecting member 2116. The transducer 2120 receives the reflected acoustic wave (reflected wave) 2118 to be transduced into an electric signal and outputs the electric signal to a signal processing unit 2124 via the detection circuit. The signal processing unit 2124 performs signal processing such as an A/D conversion or an amplification on the input electric signal and output the electric signal to a data processing unit 2126. The data processing unit 2126 uses the input signal and obtains the subject information (characteristic information on which a difference of the acoustic impedances is reflected) as image data. Herein, the signal processing unit 2124 and the data processing unit 2126 are also collectively referred to as processing unit. A display unit 2128 displays an image based on the image data input from the data processing unit 2126.

The probe may mechanically perform scanning or may also be moved with respect to the subject by a user such as a doctor or an operator (hand-held type). It is however noted that the problem of the heat generation is more conspicuous in the hand-held type probe held by hand and operated by the user, and the exemplary embodiment is preferably applied to the hand-held type probe. In case of the apparatus using the reflected wave as illustrated in FIG. 12B, the probe that transmits the acoustic wave may separately be provided in addition to the probe that receives the acoustic wave. Furthermore, an apparatus configured to have both the functions of the apparatuses illustrated in FIGS. 12A and 12B may obtain both the subject information on which the optical characteristic value of the subject is reflected and the subject information the difference in the acoustic impedances is reflected. In this case, the transducer 2020 of FIG. 12A may conduct not only the reception of the photoacoustic wave but also the transmission of the acoustic wave and the reception of the reflected wave.

According to the exemplary embodiment of the present invention, the heat generation inside the detection circuit for the transducer, the probe provided with the detection circuit, and the like can be suppressed, and it is possible to provide the detection circuit, the ultrasonic probe, and the like in which the temperature increase hardly occurs.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-047423 filed Mar. 9, 2013 and No. 2014-019964 filed Feb. 5, 2014, which are hereby incorporated by reference herein in their entirety.

What is claimed is:

1. A probe comprising:
   a transducer configured to:
      transmit an acoustic wave;
      receive a reflected acoustic wave; and
      output a detection signal in response to receiving the reflected acoustic wave;
   a detection circuit configured to:
      receive the detection signal from the transducer; and
      perform, an operation on the detection signal; and
   an operation control unit configured to output an operation signal to the detection circuit based on a transmission operation signal,
   wherein the transmission operation signal causes the transducer to transmit the acoustic wave,
   wherein the transducer and the detection circuit are installed in built-in manner, and
   wherein the detection circuit is caused to perform the operation, by the operation signal, for a first period of time, and caused to not perform the operation, by the operation signal, for a second period of time.

2. The probe according to claim 1, wherein the first period of time is when the transducer receives the reflected acoustic wave, and the second period of time is when the transducer does not receive the reflected acoustic wave.

3. The probe according to claim 1, wherein the first period of time is when the transducer is open to receiving the reflected acoustic wave, and the second period of time is when the transducer is not open to receiving the reflected acoustic wave.

4. The probe according to claim 1, wherein the detection circuit includes a transimpedance circuit serving as a current-voltage conversion circuit used for an electrostatic capacitance type element.

5. The probe according to claim 1, wherein the detection circuit includes a voltage amplification circuit used for a piezoelectric element.

6. The probe according to claim 1, further comprising:
   a transmission signal detection unit configured to output a transmission detection signal to the operation control unit based on the transmission operation signal,
   wherein the operation by the detection circuit is controlled on the basis of the transmission detection signal from the transmission signal detection unit.

7. The probe according to claim 6, further comprising:
   an operation signal generation unit configured to generate the transmission operation signal,
   wherein the operation by the detection circuit is controlled on the basis of the transmission operation signal from the operation signal generation unit.

8. The probe according to claim 6, further comprising:
   a protection switch configured to disconnect a connection between the transducer and the detection circuit when the transmission signal applied to the transducer is higher than or equal to a certain value,
   wherein the operation by the detection circuit is controlled on the basis of disconnection information of the protection switch.

9. The probe according to claim 1,
   wherein the detection circuit has a power feeding terminal configured to be supplied with a feeding power from a power source, and
   wherein the power feeding terminal is not supplied with the feeding power during the second period in which the operation signal is caused to not perform the operation.

10. The probe according to claim 9,
    wherein the detection circuit includes an input section and an output section, and
    wherein the feeding power is a feeding current or a feeding voltage to at least any one of the input section and the output section.

11. The probe according to claim 1, further comprising:
    a light source drive unit configured to drive a light source and output an irradiation synchronization signal to the operation control unit,
    wherein the operation by the detection circuit is controlled based on the irradiation synchronization signal.

12. The probe according to claim 1, further comprising:
    a light emission detection unit configured to detect light emission from a light source and output a light emission detection signal to the operation control unit,
    wherein the operation by the detection circuit is controlled on the basis of the light emission detection signal from the light emission detection unit.

13. The probe according to claim 1,
    wherein the detection circuit includes an FET source follower circuit having an operation amplifier with a VCC terminal,
    wherein the FET source follower circuit includes a switch configured to select ON/OFF in a power supply status to the VCC terminal, and
    wherein the switch is configured to be controlled by the operation control unit.

14. The probe according to claim 1,
    wherein the detection circuit includes a transimpedance circuit having an operation amplifier with a bipolar power feeding terminals V+ and V−, wherein the transimpedance circuit includes a switch configured to select ON/OFF in a power supply status to at least any one of the bipolar power feeding terminals V+ and V−, and wherein the switch is configured to be controlled by the operation control unit.

15. A subject information acquiring apparatus comprising:
a probe comprising:
   a transducer configured to:
      transmit an acoustic wave;
      receive a reflected acoustic wave; and
      output a detection signal in response to receiving the reflected acoustic wave;
   a detection circuit configured to:
      receive the detection signal from the transducer; and
      perform, an operation on the detection signal; and
   an operation control unit configured to output an operation signal to the detection circuit based on a transmission operation signal, wherein the transmission operation signal causes the transducer to transmit the acoustic wave,
   wherein the transducer and the detection circuit are installed in built- in manner, and
   wherein the detection circuit is caused to perform the operation, by the operation signal, for a first period of time, and caused to not perform the operation, by the operation signal, for a second period of time; and
a processing unit configured to obtain information of a subject by using a detection output signal from the detection circuit.

16. A driving method for a probe having a transducer, a detection circuit, and an operational control unit, wherein the transducer and detection circuit are configured in a built-in manner, the driving method comprising:
   transmitting, by the transducer, an acoustic wave;
   receiving, by the transducer, a reflected acoustic wave;
   outputting, by the transducer, a detection signal to the detection circuit;
   receiving, by the detection circuit, the detection signal outputted from the transducer;
   performing, by the detection circuit, an operation on the detection signal;
   outputting, by the operational control unit, an operation signal to the detection circuit based on a transmitted operation signal, wherein the transmitted operation signal causes the transducer to transmit the acoustic wave; and
   controlling the performing, by the detection circuit, such that the operation is caused to perform the outputting, by the operation signal, for a first period of time, and caused to not perform, by the operation signal, for a second period of time.

17. The method of claim 16, wherein controlling the operation, by the detection circuit, is caused to perform during the first period of time when the transducer receives the reflected acoustic wave, and caused to perform during the second period of time when the transducer does not receive the reflected acoustic wave.

18. The method of claim 16, wherein controlling the operation, by the detection circuit, is caused to perform during the first period of time when the transducer is open to receiving the reflected acoustic wave, and caused to perform during the second period of time when the transducer is not open to receiving the reflected acoustic wave.

19. The method of claim 16, further comprising:
   outputting a transmission detection signal to the operation control unit based on the transmission operation signal, incorporating a transmission signal detection unit; and
   controlling the detection of the detection circuit is controlled based on the transmission detection signal from the transmission signal detection unit.

20. The method of claim 16, further comprising:
   driving a light source, by a light source drive unit, for outputting an irradiation synchronization signal to the operation control unit; and
   controlling the operation by the detection circuit based on the irradiation synchronization signal.

21. The method of claim 16, wherein detection by the detection circuit includes feeding power from a power feeding terminal configured to supply power from a power source, and
   wherein the power feeding terminal is not supplied with the feeding power during the second period in which the operation signal is caused to not perform the operation.

22. The method of claim 21:
   wherein operation, by the detection circuit, is through an input section or an output section, and
   wherein feeding power to the power feeding terminal includes feeding current or a feeding voltage to at least any one of the input section and the output section.

* * * * *